(12) United States Patent
McHugo et al.

(10) Patent No.: US 8,986,363 B2
(45) Date of Patent: *Mar. 24, 2015

(54) PROXIMAL RELEASE DELIVERY SYSTEM

(75) Inventors: Vincent McHugo, Tipperary (IE); Donagh O'Sullivan, Tipperary (IE)

(73) Assignee: Cook Medical Technologies LLC, Bloomington, IN (US)

( * ) Notice: Subject to any disclaimer, the term of this patent is extended or adjusted under 35 U.S.C. 154(b) by 393 days.

This patent is subject to a terminal disclaimer.

(21) Appl. No.: 12/973,311

(22) Filed: Dec. 20, 2010

(65) Prior Publication Data

US 2012/0053671 A1    Mar. 1, 2012

Related U.S. Application Data

(60) Provisional application No. 61/291,066, filed on Dec. 30, 2009.

(51) Int. Cl.
| | | |
|---|---|---|
| *A61F 2/958* | (2013.01) | |
| *A61F 2/95* | (2013.01) | |
| *A61F 2/966* | (2013.01) | |

(52) U.S. Cl.
CPC . *A61F 2/966* (2013.01); *A61F 2/95* (2013.01); *A61F 2002/9511* (2013.01); *A61F 2002/9517* (2013.01); *A61F 2002/9665* (2013.01)
USPC .............................. 623/1.11; 606/108; 604/61

(58) Field of Classification Search
USPC ....................... 606/108; 623/1.11, 1.12, 1.23; 604/507–508, 51; 74/422, 74/89.17–89.19, 498–500
See application file for complete search history.

(56) References Cited

U.S. PATENT DOCUMENTS

| | | | | |
|---|---|---|---|---|
| 5,415,664 A | * | 5/1995 | Pinchuk | 623/1.11 |
| 5,693,083 A | * | 12/1997 | Baker et al. | 623/1.11 |
| 5,968,052 A | * | 10/1999 | Sullivan et al. | 623/1.11 |
| 5,980,533 A | * | 11/1999 | Holman | 623/1.11 |
| 6,273,917 B1 | | 8/2001 | Inoue | |
| 6,371,979 B1 | * | 4/2002 | Beyar et al. | 623/1.12 |
| 6,398,802 B1 | * | 6/2002 | Yee | 623/1.13 |
| 6,589,273 B1 | * | 7/2003 | McDermott | 623/1.11 |

(Continued)

FOREIGN PATENT DOCUMENTS

| | | |
|---|---|---|
| DE | 102 19 194 B4 | 11/2003 |
| WO | WO 2009 012061 A1 | 1/2009 |
| WO | WO 2010 078352 A1 | 7/2010 |

OTHER PUBLICATIONS

International Search Report and Written Opinion of International Searching Authority corresponding PCT Application PCT/US2010/061238, Mar. 3, 2011, 11p.

*Primary Examiner* — Darwin Erezo
*Assistant Examiner* — Richard Louis
(74) *Attorney, Agent, or Firm* — Brinks Gilson & Lione

(57) ABSTRACT

A delivery device for proximally releasing an expandable prosthesis and method of use thereof are described. The delivery device comprises an introducer sheath that is capable of distally advancing relative to the endoprosthesis to thereby expose the endoprosthesis from a proximal end thereof. The device is also capable of resheathing over the prosthesis in a proximal direction. The device comprises a drive pulley that can engage a particular gear set to axially move the introducer sheath and proximally release the prosthesis. The drive pulley can also engage another gear set to resheath the introducer sheath and recapture the prosthesis between the inner catheter and the introducer sheath. A directional switch enables the device to operate between the two modes.

20 Claims, 32 Drawing Sheets

(56) References Cited

U.S. PATENT DOCUMENTS

| | | | |
|---|---|---|---|
| 6,858,034 B1 * | 2/2005 | Hijlkema et al. | 606/108 |
| 7,803,177 B2 | 9/2010 | Hartley et al. | |
| 7,887,573 B2 | 2/2011 | Haverkost et al. | |
| 2003/0163155 A1 * | 8/2003 | Haverkost et al. | 606/194 |
| 2004/0006380 A1 * | 1/2004 | Buck et al. | 623/1.11 |
| 2004/0133273 A1 * | 7/2004 | Cox | 623/2.11 |
| 2005/0125051 A1 * | 6/2005 | Eidenschink et al. | 623/1.12 |
| 2005/0149159 A1 * | 7/2005 | Andreas et al. | 623/1.11 |
| 2007/0043381 A1 * | 2/2007 | Furst et al. | 606/108 |
| 2007/0060999 A1 * | 3/2007 | Randall et al. | 623/1.11 |
| 2007/0270784 A1 * | 11/2007 | Smith et al. | 606/1 |
| 2008/0300613 A1 * | 12/2008 | Shelton et al. | 606/170 |
| 2008/0319524 A1 * | 12/2008 | Yachia et al. | 623/1.11 |
| 2009/0024133 A1 * | 1/2009 | Keady et al. | 606/99 |
| 2010/0004606 A1 * | 1/2010 | Hansen et al. | 604/264 |

\* cited by examiner

PROXIMAL RELEASE DELIVERY SYSTEM

CROSS-REFERENCE TO RELATED APPLICATIONS

The present application claims the benefit of U.S. Provisional Application No. 61/291,066, titled "Proximal Release Delivery Device", filed Dec. 30, 2009, the entirety of which is hereby incorporated by reference.

TECHNICAL FIELD

This invention relates to a medical device and, in particular to a device for delivering and deploying a self-expandable prosthesis and a method of delivering and deploying the prosthesis into a body lumen.

BACKGROUND

A self-expanding prosthesis is typically introduced into the body using a delivery device that comprises a push-pull mechanism. The delivery device comprises an outer catheter coaxially disposed and slidable over an inner catheter. The prosthesis is disposed at the distal end of the device between the inner catheter and the outer catheter. The inner and the outer catheter move coaxially with respect to each other. The prosthesis may be deployed by proximally pulling back the outer catheter relative to the inner catheter until the prosthesis is exposed.

There are numerous drawbacks to the above push-pull delivery device. For example, utilizing a conventional push-pull delivery device may cause the physician to inadvertently use excessive force and pull back the outer catheter too far, thereby prematurely deploying the prosthesis in an incorrect position within a body lumen. At this step in the procedure, repositioning of the prosthesis becomes difficult, if not impossible, because the prosthesis has already radially self-expanded into the body lumen. Additionally, retraction of the outer sheath may not be achieved with controlled movement because the physician is manually retracting the outer catheter. Manual retraction of the outer catheter may lead to inadvertent jerking of the outer catheter. Furthermore, two hands are typically needed to deploy the prosthesis with a push-pull mechanism. One hand may be required to hold the inner catheter while the other hand pulls the outer catheter and slides it back over the inner catheter. The use of two hands prevents the physician from performing another task during the procedure.

Additionally, in a typical push-pull device, the first portion of the self-expanding stent to make contact with the body vessel is the most distal portion of the stent because the sheath is pulled away from the stent in the proximal direction. This type of system may also be referred to as a "distal release" device. Distal release devices generally allow for accurate placement of the distal portion of a self-expanding stent, but often do not allow for accurate placement of the proximal portion of a stent.

Accurate placement of the proximal portion of the stent may be important in certain applications. For example, the deployment of self-expanding stents within the gastrointestinal (GI) tract is well-known. However, the use of a distal release device may prevent accurate placement of the proximal portion of the stent. As an example, foreshortening stents tend to anchor within the GI tract at the initial location that the stent makes contact with the body vessel and thereafter shorten away from that location along a central axis of the stent. Thus, when using a foreshortening stent, the distal end that initially opens is relatively easy to place with accuracy, but the final location towards the opposite proximal end of the stent is variable, oftentimes being dependent upon the extent to which the deployed stent elongates within a lumen of the target stricture. The amount of elongation may be dependent on the lumen and stricture size. Accordingly, accurate positioning of the proximal end of a foreshortening stent that is distally released may not be possible.

In some applications, there is a clinical need to achieve placement of the proximal end of the self-expanding stent that is more accurate than conventional distal release devices. For example, when there is a need to deploy a self-expanding stent at a relatively more proximal region within the esophageal region, the proximal end of the stent should ideally be deployed above the stricture but below the cricopharyngeal region of the throat to avoid aggravation of the nerves that control the coughing response. Such a need for deployment at a relatively more proximal region within the esophagus may occur when strictures along the proximal portion of the esophagus develop following surgical esophagectomy. Additionally, malignant lesions that develop proximally in the esophagus may also be treated with self-expanding stents capable of being accurately deployed along their proximal ends.

Accordingly, in view of the drawbacks of current technology, there is a desire for a proximal release delivery system that can increase the control, accuracy and ease of placement during deployment of the prosthesis. The proximal release device may reduce the risk of malfunction, provide for ease of deployment, and allow the ability to recapture the stent after partial deployment. Although the embodiments described below may be useful for increasing the control, accuracy and ease of placement during proximal release of the prosthesis, the claimed inventions may also solve other problems.

SUMMARY

Accordingly, a delivery device is provided comprising an outer catheter that is capable of retracting in a distal direction and resheathing over the prosthesis in a proximal direction.

The invention may include any of the following aspects in various combinations and may also include any other aspect described below in the written description or in the attached drawings.

In a first aspect, a device for deploying an intraluminal device is provided. The device comprises a gear and pulley mechanism comprising a first gear set and a second gear set. A drive pulley is adapted to be mechanically coupled to one of the first gear set and the second gear set. An introducer sheath is operably connected to the drive pulley. An expandable prosthesis is constrained within the introducer sheath. The sheath is movable in a distal direction relative to the prosthesis when the drive pulley is mechanically coupled to the first gear set so as to release the prosthesis from a proximal end thereof. The sheath is retractable in a proximal direction relative to the prosthesis when the drive pulley is mechanically coupled to the second gear set so as to resheath over the prosthesis.

In a second aspect, a device for delivering an intraluminal device is provided. A housing is provided comprising a gear and pulley mechanism. The mechanism further comprises a first gear set and a second gear set. A drive pulley is adapted to be mechanically coupled to one of the first gear set and the second gear set. An elongate member is fixably connected to a distal end of the housing. An expandable prosthesis has a first proximal end and a first distal end. The prosthesis is mounted over a distal portion of the inner elongate member. A stabilizing assembly secures the first distal end of the prosthesis to the inner elongate member. An introducer sheath is axially movable over the prosthesis. The sheath has a second distal end positioned distal to the first distal end of the prosthesis and a second proximal end positioned proximal to the first proximal end of the prosthesis. The sheath is operably connected to the drive pulley so as to allow the second proximal end of the sheath to slidably advance distally relative to the first proximal end of the prosthesis to thereby expose a proximal portion of the prosthesis.

In a third aspect, a device for delivering an intraluminal device is provided. The device comprises a first gear set and a second gear set. A drive pulley is adapted to be alternatively mechanically coupled to the first gear set and the second gear set. A belt is coupled to the drive pulley. An introducer sheath is mechanically coupled to the belt. An expandable prosthesis is constrained within the introducer sheath. The belt is configured to rotate in a clockwise direction when the drive pulley is mechanically coupled to the first gear set to distally advance the sheath beyond a proximal end of the prosthesis so as to release a proximal portion of the prosthesis from within the sheath. The belt is also configured to rotate in a counterclockwise direction when the drive pulley is mechanically coupled to the second gear set to proximally retract the sheath over the prosthesis.

BRIEF DESCRIPTION OF THE DRAWINGS

Embodiments will now be described by way of example with reference to the accompanying drawings, in which:

FIG. 33 shows a cross-sectional view of a reinforced outer sheath;

DETAILED DESCRIPTION OF THE EMBODIMENTS

Figure 1:
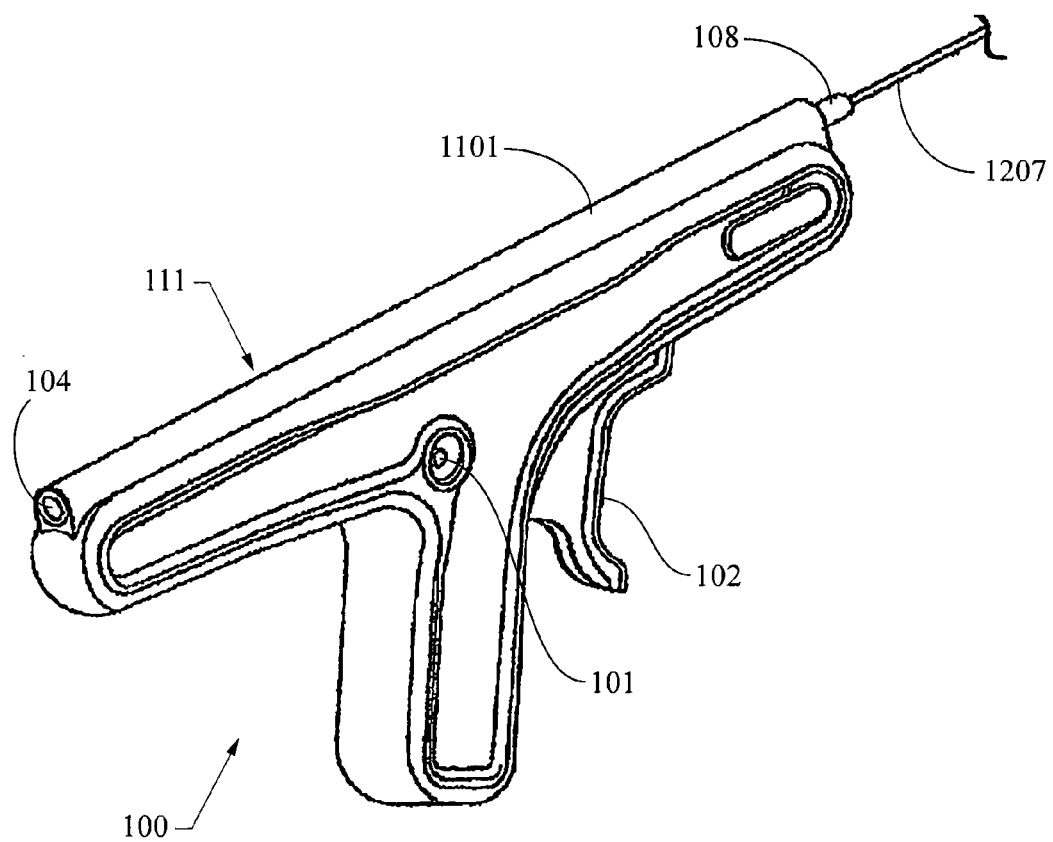
FIG. 1 is a perspective view of a proximal release delivery device.

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted, which are not necessary for an understanding of the embodiments, such as conventional details of fabrication and assembly.

Throughout the specification, the terms "distal" and "distally" shall denote a position, direction, or orientation that is generally away from the physician. Accordingly, the terms "proximal" and "proximally" shall denote a position, direction, or orientation that is generally towards the physician.

The term "crown" as used throughout the specification includes struts of an endoprosthesis forming the edges thereof.

Referring now to the drawings in FIGS. 1-42, a delivery device for deploying a self-expanding prosthesis is shown. As will be discussed, the delivery device proximally releases the prosthesis, and can also resheath and reposition the prosthesis as needed. The delivery device as will be described below may substantially increase the control and accuracy of the deployment process compared to conventional delivery devices.

Figure 31:
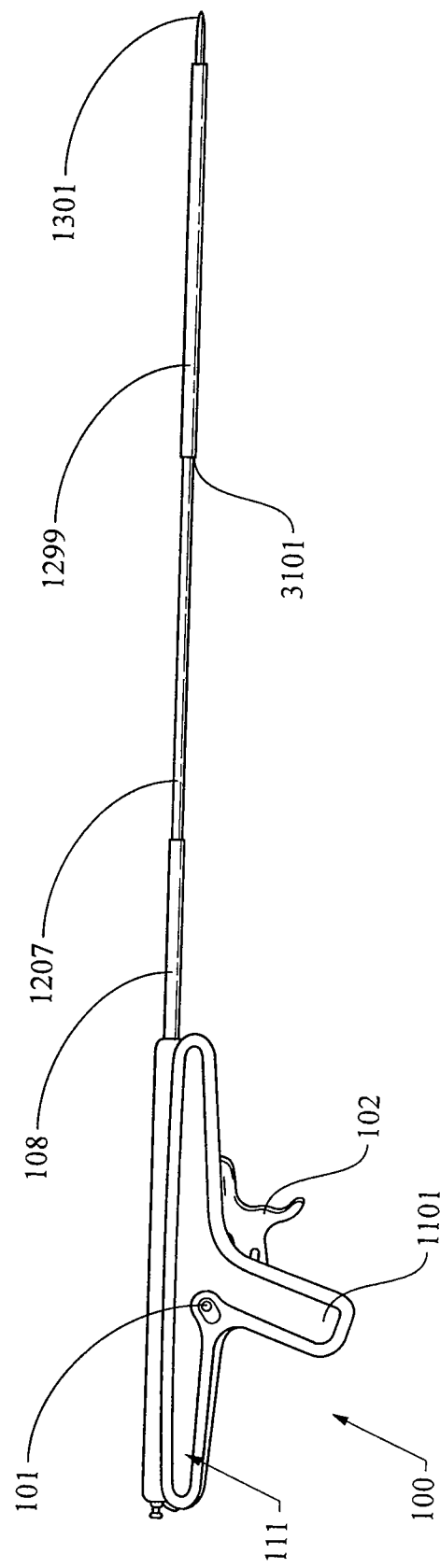
FIG. 31 shows the handle affixed to the inner catheter and introducer sheath with an endoprosthesis loaded within the introducer sheath.

FIGS. 1 and 31 show an embodiment of a proximal release delivery device 100. Actuation of a spring-loaded trigger 102 (FIG. 1) pushes the introducer sheath 1299 in the distal direction relative to the inner catheter 1207 (shown in FIG. 32) to expose a self-expanding prosthesis 301 (FIG. 32) from a proximal end 309 thereof. FIGS. 1 and 31 additionally show that a directional switch 101 may be engaged, prior to actuating the trigger 102, to control the direction of movement of the introducer sheath 1299. An internal gear-pulley mechanism, which will be explained in greater detail below, enables bi-directional axial movement of the introducer sheath 1299. Generally speaking, the directional switch 101 can be pressed so as to engage the gear-pulley mechanism in a first configuration that causes distal movement of the sheath 1299 relative to inner catheter 1207, thereby causing deployment of the prosthesis 301 from the proximal end 309 thereof, as shown by the arrows in FIG. 32. When the directional switch 101 is pressed in the opposite direction, the gear-pulley mechanism is engaged in a second configuration that causes proximal movement of the sheath 1299 relative to the inner catheter 1207, thereby causing the introducer sheath 1299 to resheath over the prosthesis 301, as shown by the arrows in FIG. 33.

Figure 32:
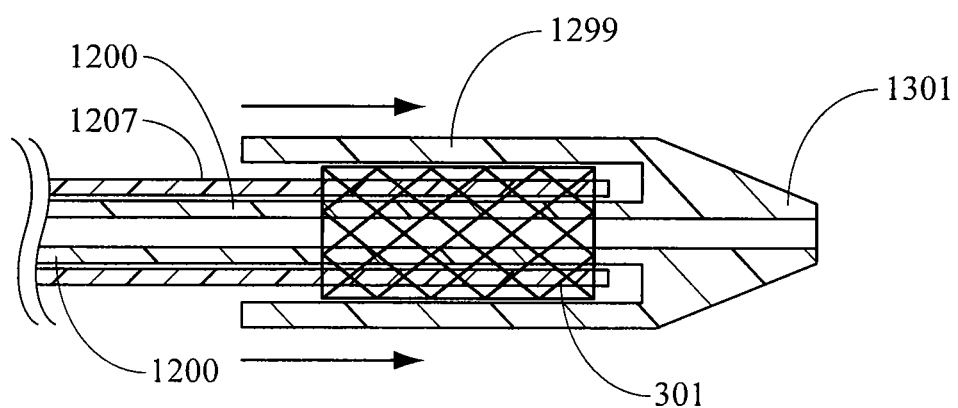
FIG. 32 shows a cross-sectional view of the introducer sheath axially moveable in the distal direction relative to the inner catheter to proximally release an endoprosthesis.
Figure 33:
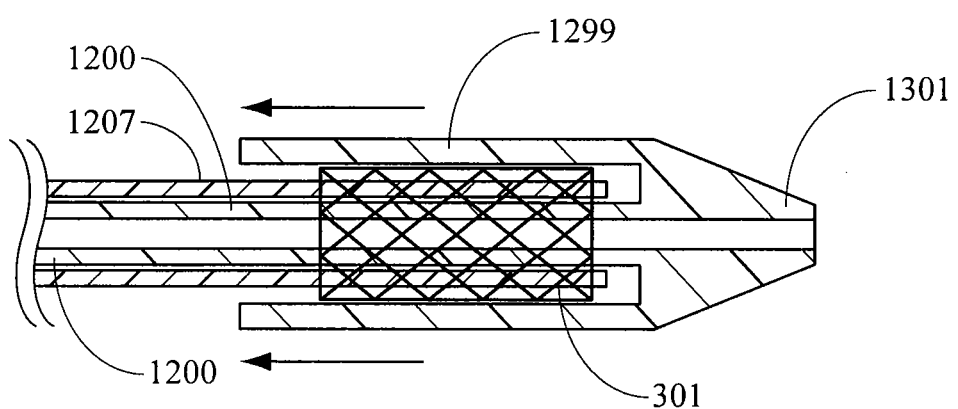
FIG. 33 shows a cross-sectional view of the introducer sheath axially moveable in the proximal direction relative to the inner catheter to resheath over the endoprosthesis.

One example of a design for the proximal release mechanism includes two concentric tubes in which an inner cannula 1200 extends within the luminal space of an inner catheter 1207 (FIGS. 32 and 33). The endoprosthesis is mounted on the distal portion of the inner catheter 1207. Movement of the inner cannula 1200 via the gear and pulley system, located in the interior of the housing 1101 of the handle 111, causes the introducer sheath 1299 to slidably move back and forth over the endoprosthesis 301, thereby allowing proximal release and resheathing of the endoprosthesis 301.

The components of the proximal release mechanism will now be described. The distal portion of the inner catheter 1207, which is shown in FIGS. 32 and 33, is coaxially disposed within the sheath 1299. This portion of the inner catheter 1207 serves as the supporting rail onto which endoprosthesis 301 is mounted thereon. FIGS. 1 and 31 show that the inner catheter 1207 is fixably connected to a nozzle 108 at the distal end of the housing 1101 of the delivery device 100. The inner catheter 1207 extends distally from the distal end of the housing 1101 of the handle 111 (FIG. 31), through the luminal space of the endoprosthesis 301 (FIGS. 32 and 33), and thereafter terminates at about the distal tip 1301 (FIGS. 32 and 33).

The introducer sheath 1299 is shown connected to a distal tip 1301 (FIGS. 31-33), and the distal tip 1301 is shown connected to an inner cannula 1200 (FIGS. 32 and 33). In one embodiment, the sheath 1299, inner cannula 1200, and distal tip 1301 may be a unitary molded piece such that the inner cannula 1200 everts upon itself to become the introducer sheath 1299 (FIGS. 32 and 33). The introducer sheath 1299 spans at least the length of the endoprosthesis 301 so as to constrain the entire endoprosthesis 301, which is shown disposed between the introducer sheath 1299 and the inner catheter 1207 during delivery. Specifically, FIG. 31 shows that the introducer sheath 1299 may proximally extend from the distal tip 1301 to the location designated as 3101.

Figure 7:
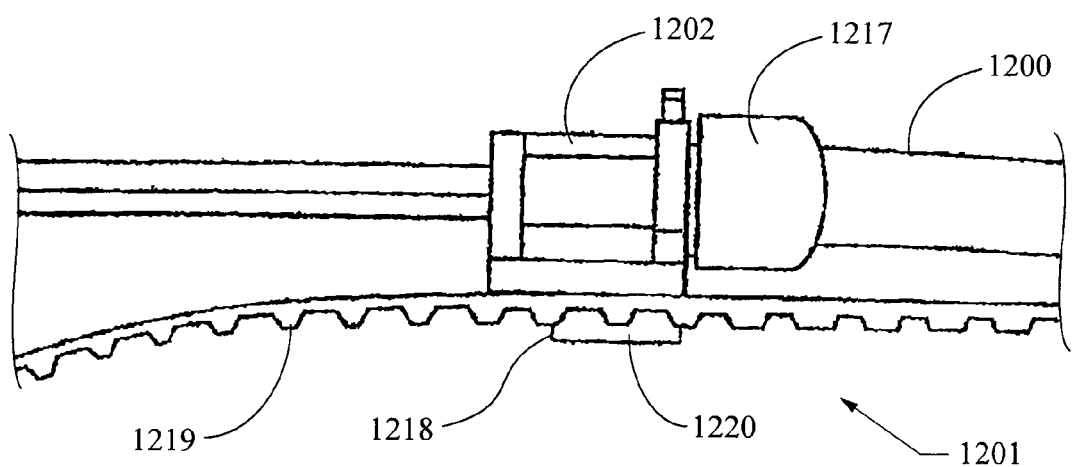
FIG. 7 shows the attachment of the belt to the shuttle and inner cannula.
Figure 34:
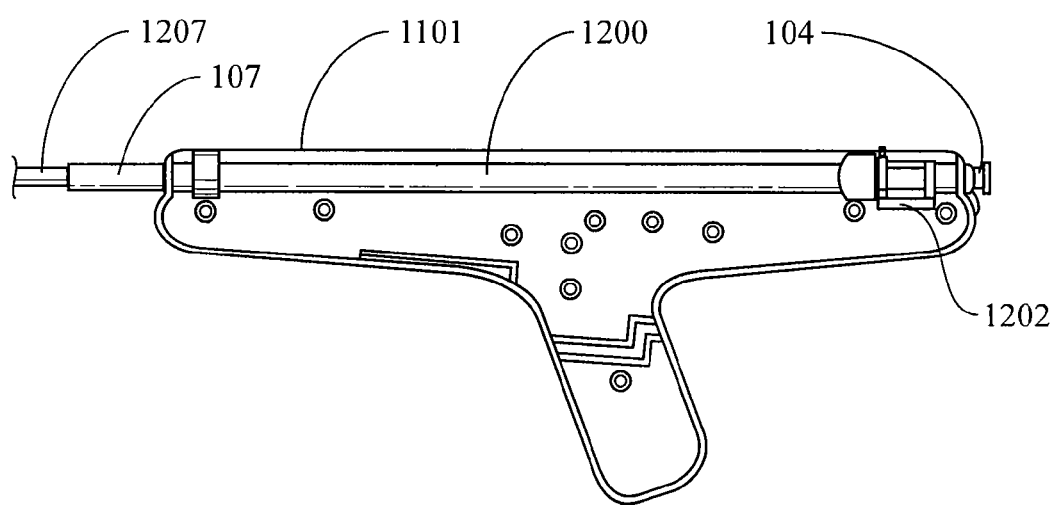
FIG. 34 shows the proximal end of the inner cannula extending affixed to the shuttle within the interior of the housing of the handle.
Figure 35:
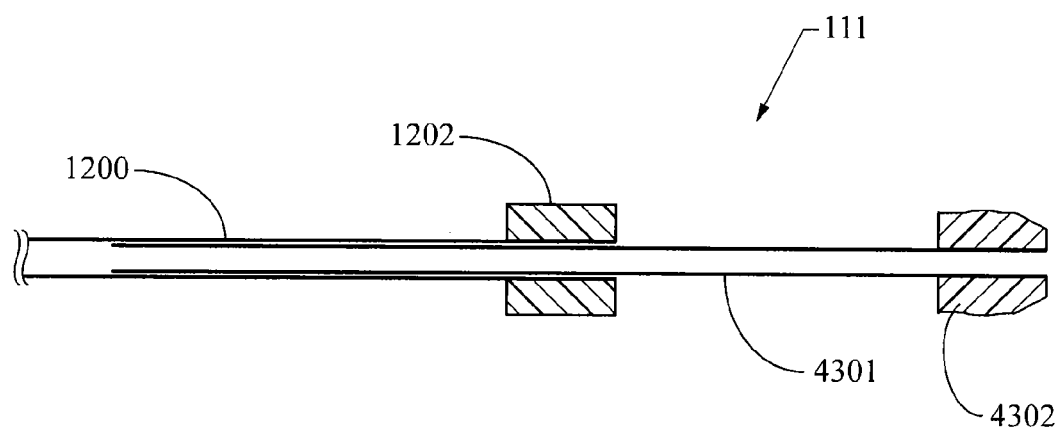
FIG. 35 shows a second cannula partially extending within the inner cannula.

Referring to FIGS. 34 and 35, the proximal end of the inner cannula 1200 is affixed to the shuttle 1202. Bi-directional movement of the shuttle 1202 (FIG. 35) via the gear-pulley mechanism enables movement of the inner cannula 1200. Because the inner cannula 1200 is shown in FIGS. 32 and 33 to be integral with the distal tip 1301 and the sheath 1299, the sheath 1299 undergoes movement in the same direction as the inner cannula 1200. The inner cannula 1200 distally extends from the shuttle 1202 and emerges from within the distal end 107 of the housing 1101 (FIG. 34). The portion of the inner cannula 1200 emerging from within the housing 1101 may extend coaxially within the luminal space of inner catheter 1207. The inner cannula 1200 continues to longitudinally extend through the lumen of the endoprosthesis 301 (FIG. 32) and thereafter terminates as the distal tip 1301. The inner cannula 1200 is connected to the belt 1201 of the gear-pulley system through the shuttle 1202, as shown in FIG. 7. Rotational movement of the belt 1201 is translated to linear movement of the inner cannula 1200. As the inner cannula 1200 is connected via the distal tip 1301 to the sheath 1299, movement of the inner cannula 1200 causes the sheath 1299 to move in the same direction.

Figure 36:
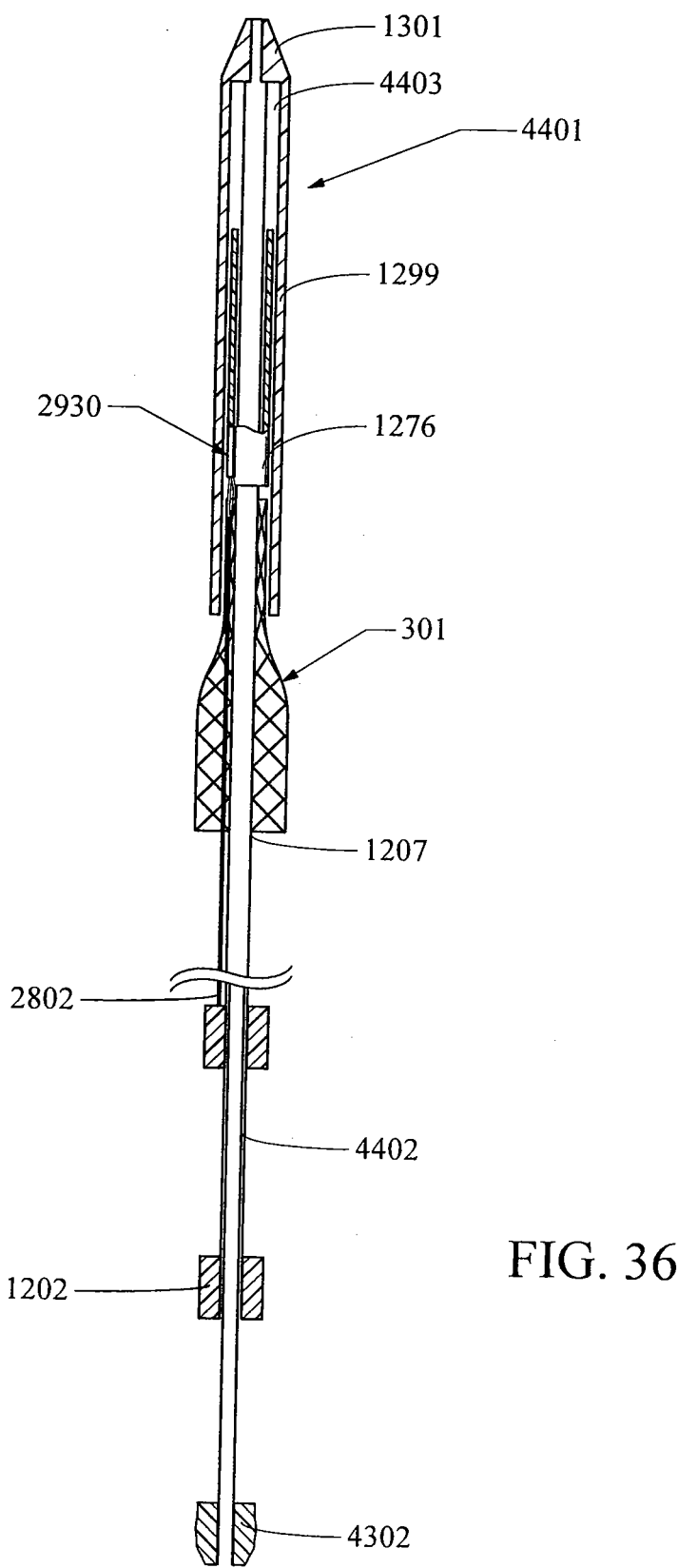
FIG. 36 shows an atraumatic outer sheath covering the introducer sheath.

FIG. 35 shows the interior of a housing 1101 of the handle 111 in which a second cannula 4301 partially extends within the inner cannula 1200. For purposes of clarity, the gearing components and belt 1201 have been omitted. The proximal end of the second cannula 4301 is stationary as it is connected to the proximal end 4302 of the housing 1101 of the handle 111, thereby allowing introduction of a wire guide, contrast injection, or other fluids to be injected therethrough. The overlapping portion of the second cannula 4301 with the inner cannula 1200 allows the wire guide and/or other fluids to extend from the distal end of the second cannula 4301 into the proximal end of the inner cannula 1200 and thereafter travel the longitudinal length of the device 100. The wire guide and fluids exit through distal tip 1301 (FIGS. 32, 33, and 36).

The device 100 may also have a sheath covering feature to cover the introducer sheath 1299. FIG. 36 shows a side view of the entire device. The sheath covering feature is shown as an atraumatic outer sheath 4401. Atraumatic outer sheath 4401 is disposed over the introducer sheath 1299. The atraumatic outer sheath 4401 may prevent trauma to the body during axial movement of the introducer sheath 1299. The sheath 4401 includes an inner portion 4402 and an outer portion 4403. The inner portion 4402 of the atraumatic outer sheath 4401 extends through both the inner cannula 1200 and the inner catheter 1207. The outer portion 4403 of the sheath 4401 extends over the distal tip 1301 and thereafter extends in the proximal direction a sufficient distance to cover the introducer sheath 1299.

Figure 2:
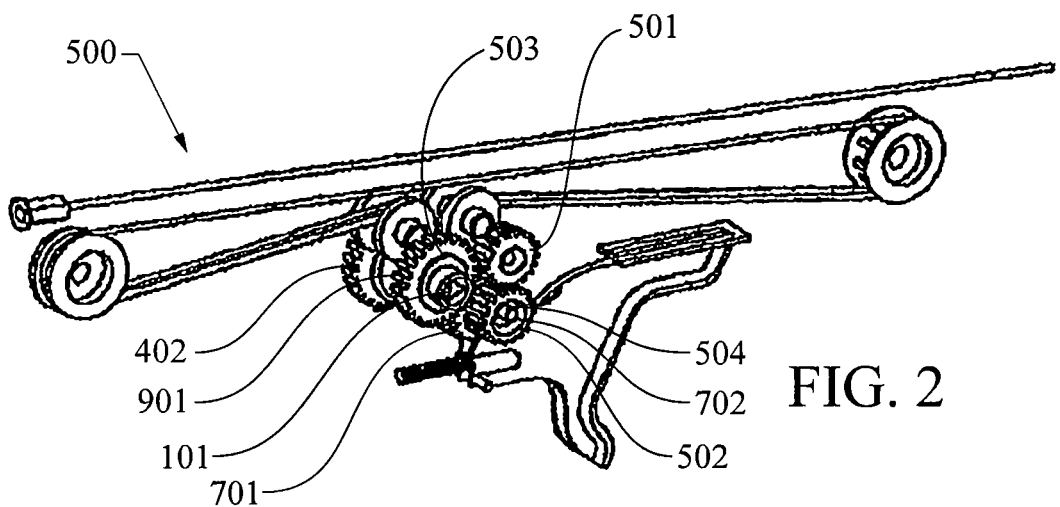
FIG. 2 is a perspective view of a first gear set of the delivery device.

The details by which bi-directional axial movement of the introducer sheath 1299 occurs via rotational movement of the belt 1201 will now be explained. Activation of a first gear set causes the introducer sheath 1299 to move distally relative to the inner catheter 1207 such that the endoprosthesis 301 is proximally released from within the sheath 1299. FIG. 2 shows the first gear set 500. The first gear set 500 comprises a first drive gear 502, a first idle gear 501, and a first pulley gear 503. The first drive gear 502 is mechanically engaged with the first idle gear 501. The first idle gear 501 is mechanically engaged with the first pulley gear 503. The first drive gear 502 has a one-directional roller clutch bearing 504. Specifically, the roller clutch bearing 504 is may be press fit within the inner surface of the first drive gear 502 and allows for rotation of the first drive gear 502 in only one direction, which will be explained in greater detail below.

Figure 3:
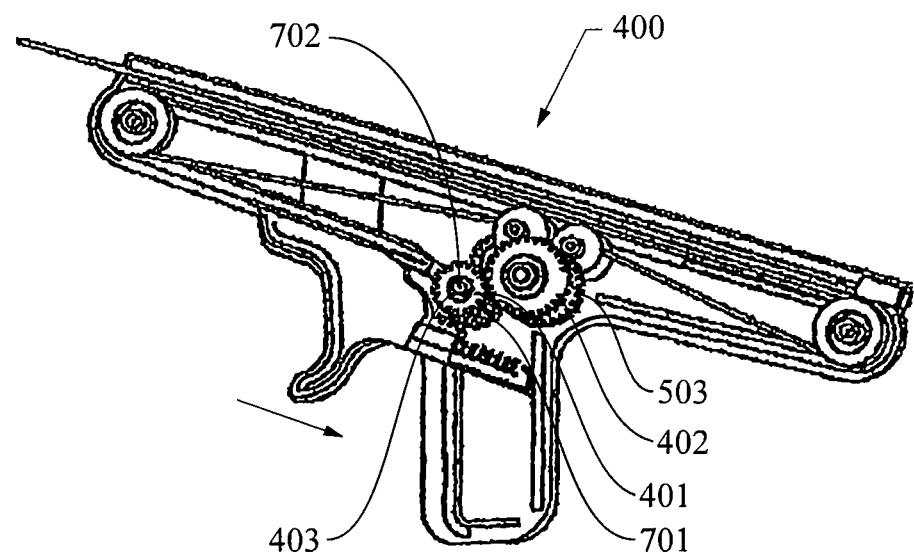
FIG. 3 is a perspective view of a second gear set of the delivery device.

Activation of a second gear set proximally retracts the introducer sheath 1299 (i.e., moves the introducer sheath 1299 in a proximal direction relative to the inner catheter 1207) so as to resheath the sheath 1299 over the endoprosthesis 301. FIG. 3 shows the second gear set 400. The second gear set 400 comprises a second drive gear 401 and a second pulley gear 402. The second drive gear 401 is mechanically coupled to the second pulley gear 402. Similar to the first drive gear 502, the second drive gear 401 also comprises a roller clutch bearing 403 that allows for rotation of the gear 401 in only one direction, which will be explained in greater detail below.

Figure 12:
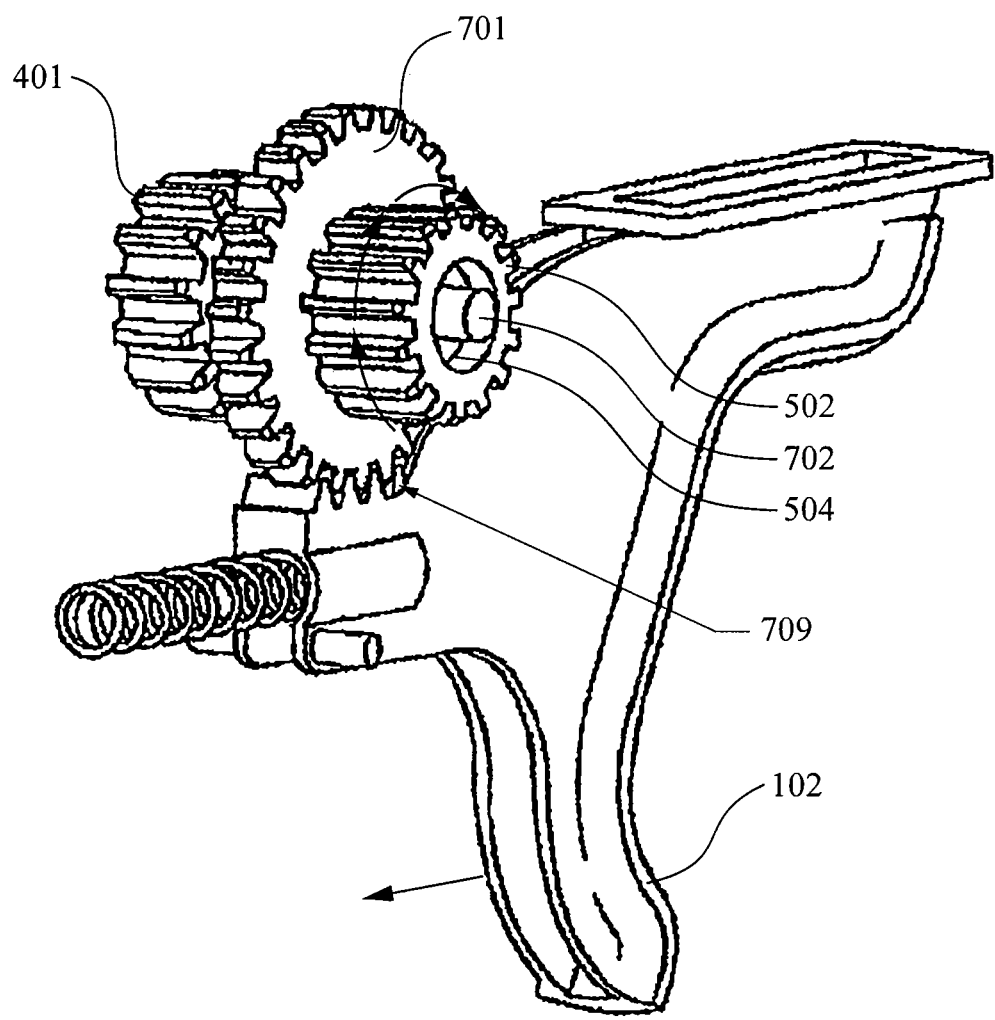
FIG. 12 shows the trigger and the drive gears.

A drive shaft 702 extends through the clutch bearing 403 of the second drive gear 401 (FIG. 3) and through the clutch bearing 504 of the first drive gear 502 (FIG. 2). A main drive gear 701 is rotationally fixed to the drive shaft 702, as clearly seen in FIG. 27. The main drive gear 701 is also engaged with a trigger 102 (FIG. 12). The trigger 102 includes a rack 709 having complimentary teeth 704 (FIG. 11) that engage with the main drive gear 701.

Figure 4:
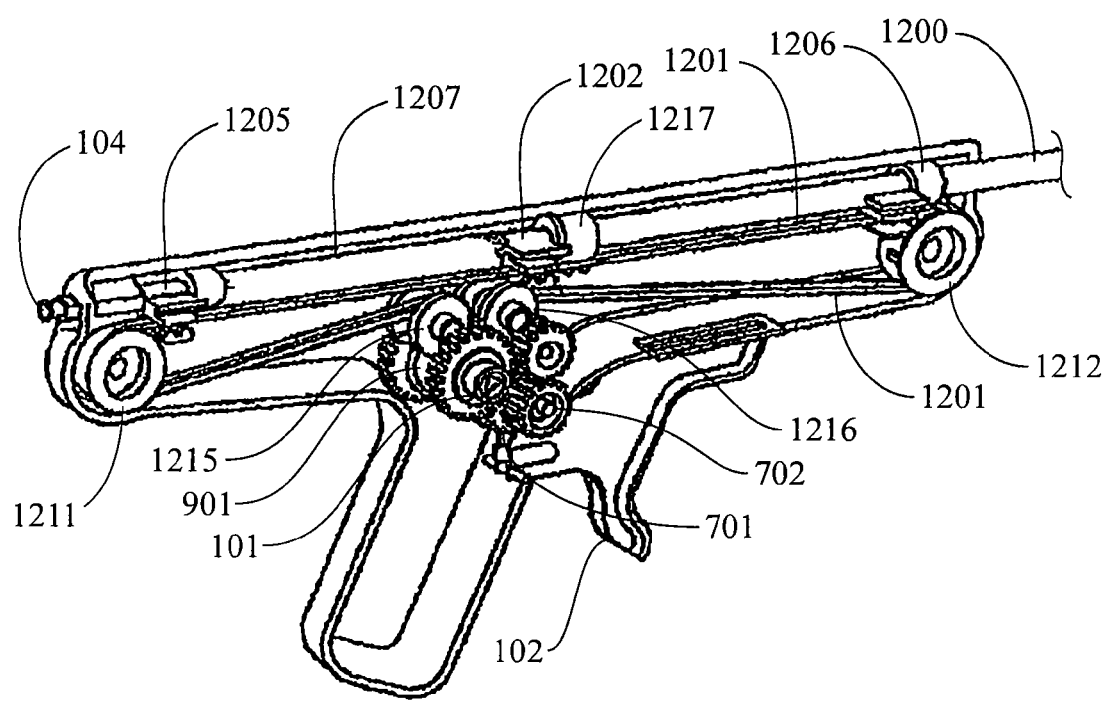
FIG. 4 is a perspective view of the delivery device showing the inner cannula connected to a belt.
Figure 5:
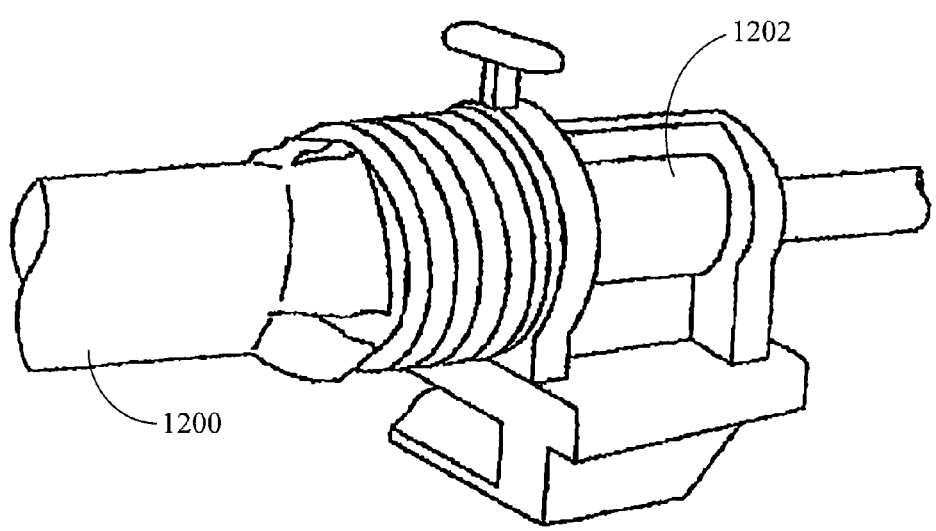
FIG. 5 shows the inner cannula affixed to a shuttle.
Figure 6:
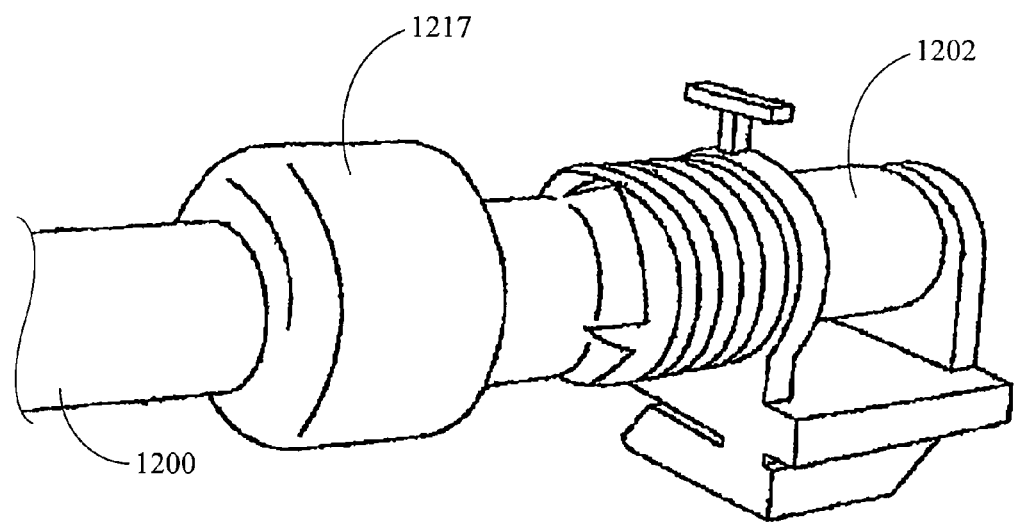
FIG. 6 shows a shuttle cap being screwed to the shuttle to secure the inner cannula to the shuttle.

Proximal and distal linear movement of the inner cannula 1200 may be achieved by the coupling of the inner cannula 1200 to the belt 1201, as shown in FIG. 4. For purposes of clarity and to illustrate movement of the inner cannula 1200 along the belt 1201 from the interior of the housing 1101 of handle 111 to the exterior thereof, FIG. 4 intentionally omits the inner catheter 1207, which otherwise would be shown coaxially disposed over the inner cannula 1200 (see FIGS. 32-34). The inner cannula 1200 is coupled to the belt 1201 by shuttle 1202. FIGS. 5 and 6 show one possible type of connection between the inner cannula 1200 and the shuttle 1202. FIG. 5 shows that the end of the inner cannula 1200 may be abutted against the shuttle 1202. After abutting the inner cannula 1200 against the shuttle 1202, FIG. 6 shows that a shuttle cap 1217 may be coupled to the shuttle 1202. Specifically, the shuttle cap 1217 may be screwed onto the threads of the shuttle 1202 to secure the inner cannula 1200 to the shuttle 1202. Other types of attachments of the inner cannula 1200 to the belt 1201 are contemplated as would be apparent to one of ordinary skill in the art. The proximal end of the inner catheter 1207 may be secured to the nozzle 108 at the distal end of the housing 1101 (FIGS. 1, 31, and 34) of device 100 in a similar manner.

The attachment of the belt 1201 to the shuttle 1202 and inner cannula 1200 may be seen in FIG. 7. FIG. 7 shows that the shuttle 1202 contains an opening 1218 through which belt 1201 may extend. The shuttle 1202 contains corresponding grooves 1220 that engage with protrusions 1219 of the belt 1201 to establish a secure belt-shuttle connection. Counter-clockwise movement of the belt 1201 causes the shuttle 1202 and inner cannula 1200 attached thereto to linearly move along the belt 1201 in the proximal direction when resheathing endoprosthesis 301. Clockwise movement of the belt 1202 causes the shuttle 1202 and inner cannula 120 attached thereto to move linearly along the belt 1201 in the distal direction to proximally releasing the endoprosthesis 301.

Referring to FIG. 4, activation of the first gear set 500 or the second gear set 400 rotates a center drive pulley 901 and the belt 1201 to cause the shuttle 1202 with the inner cannula 1200 attached thereto to move with the belt 1201. FIG. 4 illustrates possible positions of the inner cannula 1200. The most reverse position of the belt 1201 and shuttle 1202 coupled to cannula 1200 is indicated at position 1205. The most forward position of the belt 1201 and shuttle 1202 coupled to cannula 1200 is indicated at position 1206. For purposes of clarity, the shuttle cap 1217 is not shown at positions 1205 and 1206. As the inner cannula 1200 moves along the belt 1201, the inner catheter 1207 (more clearly seen in FIG. 31) remains stationary because the inner catheter 1207 is fixated at the distal end of the housing 1101 of the device 100 at nozzle 108.

Figure 8:
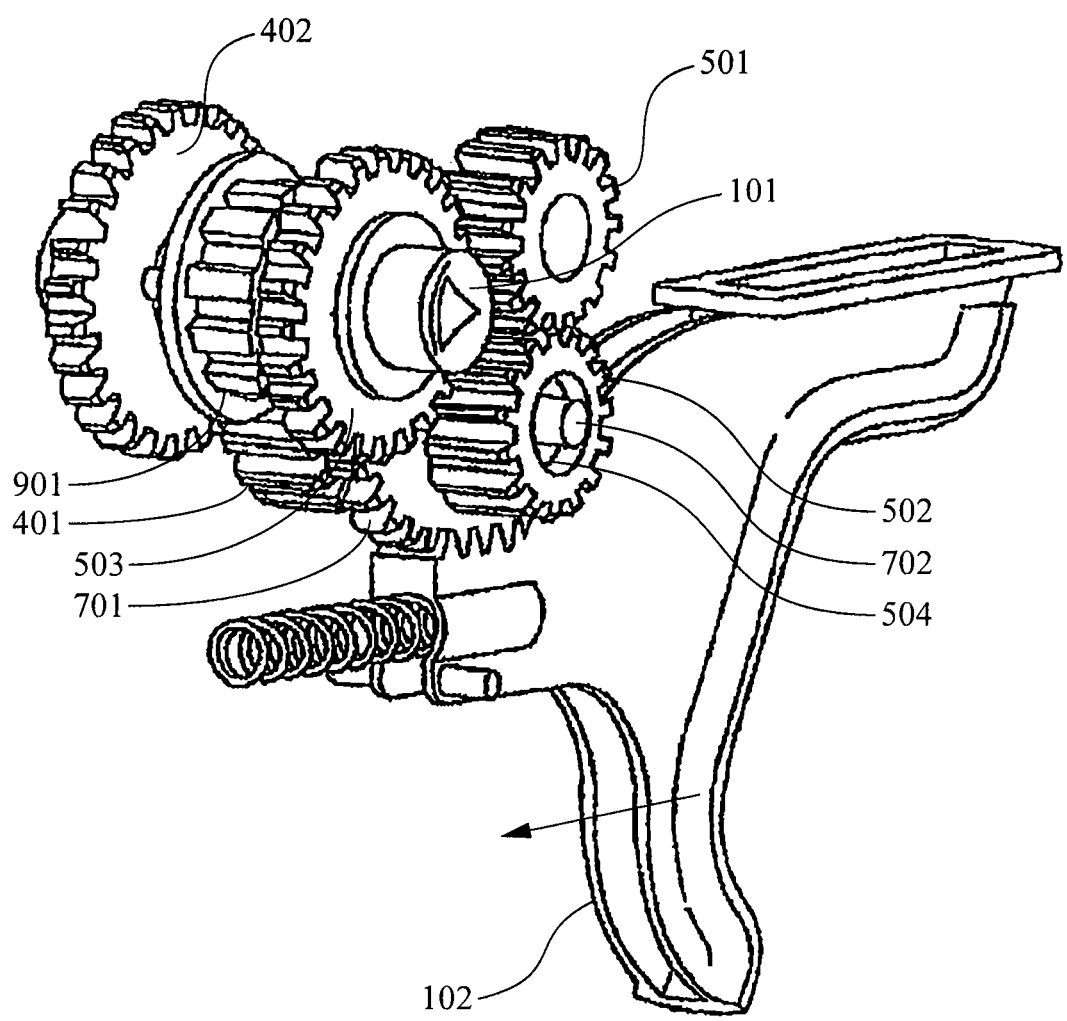
FIG. 8 shows the trigger, drive gears, and pulley gears.

Referring to FIG. 8, desired belt 1201 movement is achieved by engaging a center drive pulley 901 with the first pulley gear 503 or the second pulley gear 402. The first pulley gear 503 and the second pulley gear 402 are slidable along a shaft to engage and disengage with the drive pulley 901. The engagement and disengagement may occur by the ribs or protrusions 1000 of the pulley gears 503, 402 slidably engaging with the ribbed slots 902 of the center drive pulley 901. Directional switch 101 allows the first pulley gear 503 or the second pulley gear 402 to engage with the center drive pulley 901. Referring to FIG. 8, the first pulley gear 503, second pulley gear 402, and directional switch 101 extend along a shaft (not shown). Pushing the directional switch 101 against the first pulley gear 503 causes the first pulley gear 503 to engage with the center drive pulley 901 and the second pulley gear 402 to disengage with the center drive pulley 901 along the shaft. At any given time, the center drive pulley 901 may be engaged to either the first pulley gear 503 or the second pulley gear 402.

Figure 9:
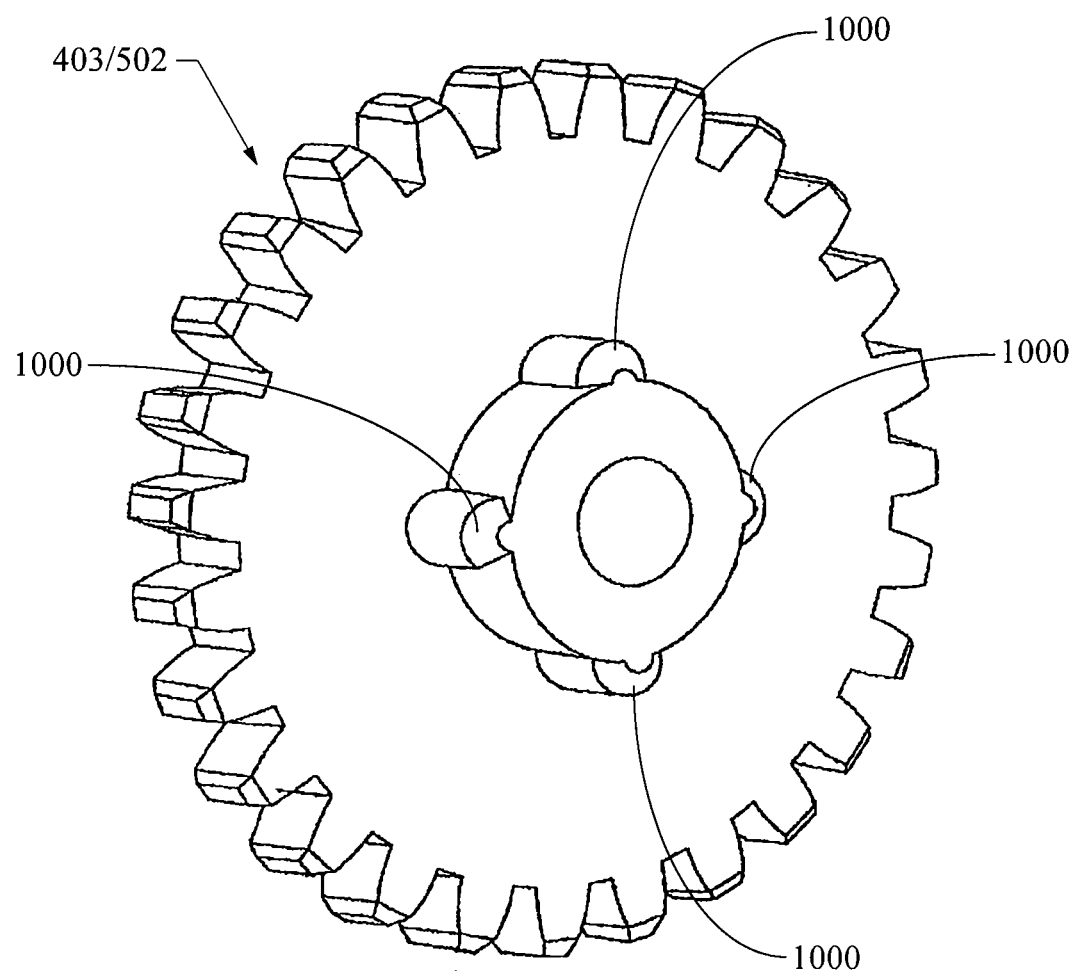
FIG. 9 shows protrusions on one of the faces of the pulley gear that is configured to slot into corresponding slotted ribs located on the center drive pulley.
Figure 10:
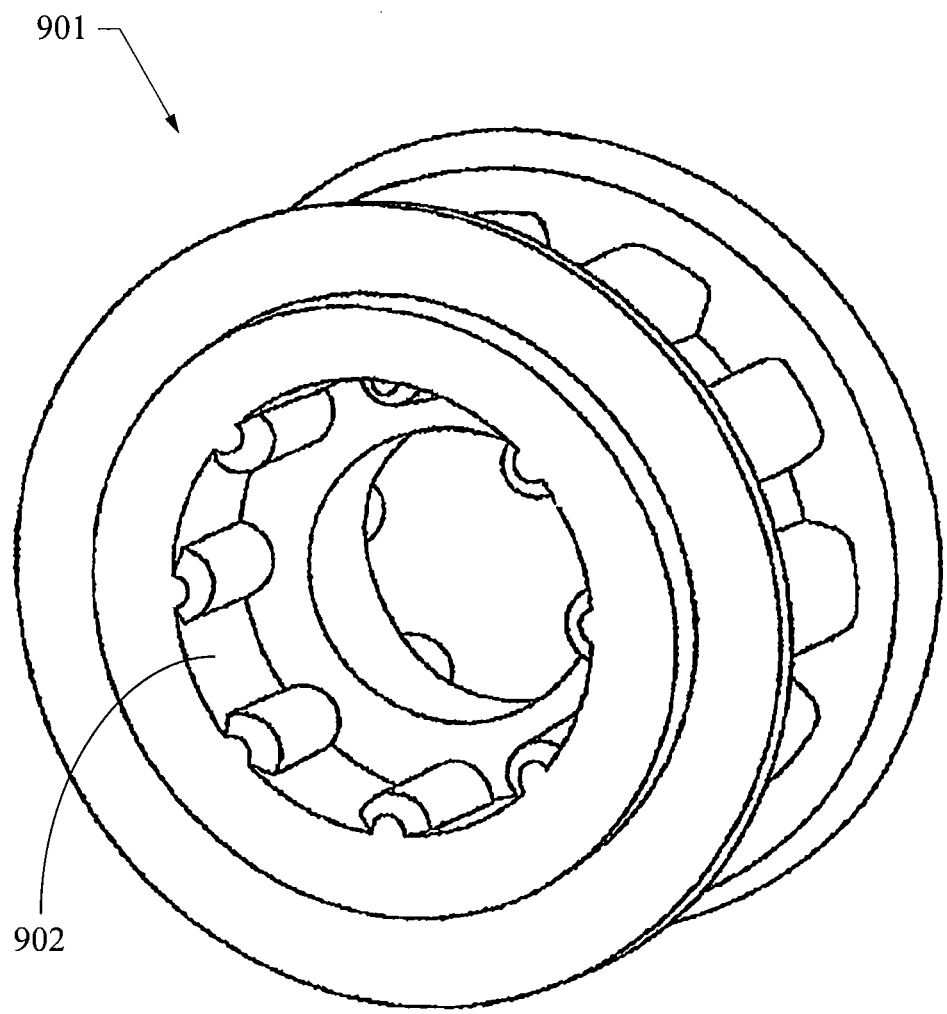
FIG. 10 shows ribbed slots on the center drive pulley that are configured to receive the pulley gears.
Figure 11:
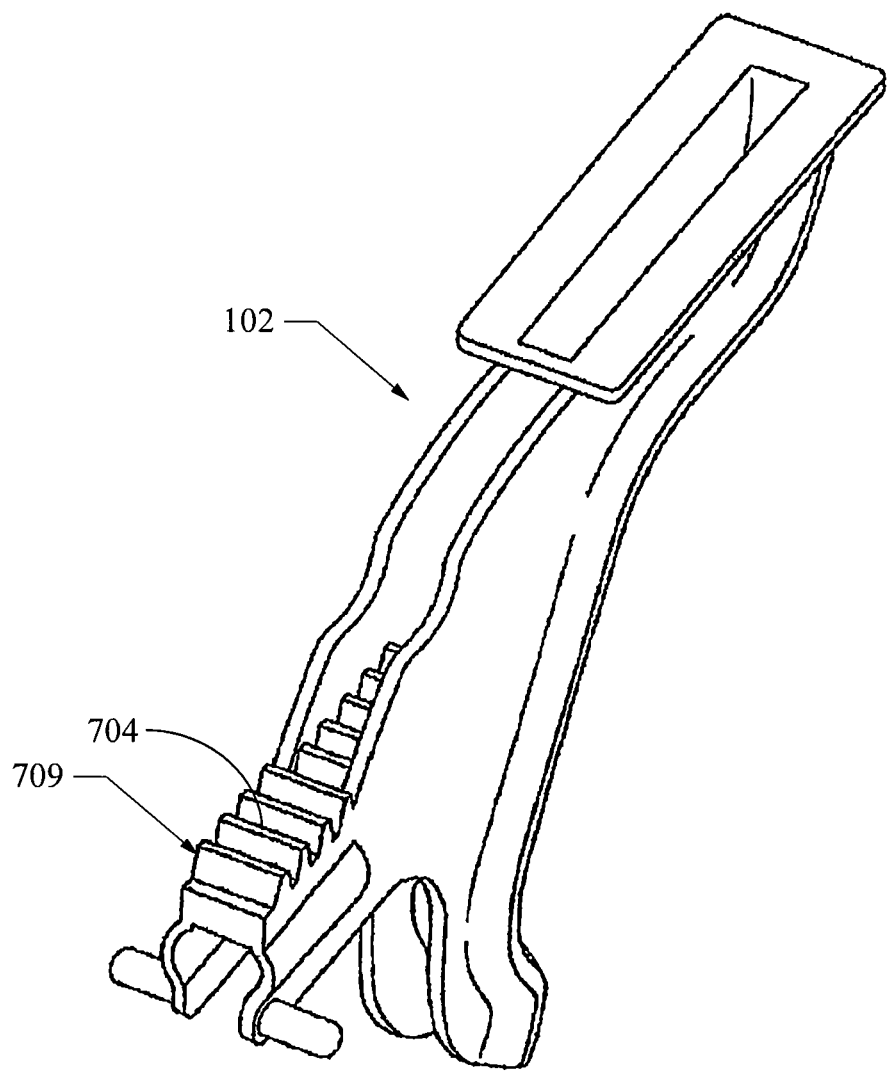
FIG. 11 shows the rack of the trigger of the delivery device.

The engagement of the first or second pulley gears 503, 402 with the center drive pulley 901 can be understood by referring to FIGS. 9 and 10. The first and second pulley gears 503 and 402 may appear as shown in FIG. 9. FIG. 10 shows that the center drive pulley 901 contains ribbed slots 902 that correspond to protrusions 1000 (FIG. 9) of the first and second pulley gears 503, 402. The multiple side protrusions 1000 of the first and second pulley gears 503, 402 (FIG. 9) slide into the ribbed slots 902 located on the side of the center drive pulley 901 (FIG. 10) to lockably engage with each other. The engagement may be such that when the locked first pulley gear 503 or locked second pulley gear 402 rotates, the center drive pulley 901 will rotate in the same direction, thereby transferring the motion of the pulley gears 503, 402 to the drive pulley 901 and belt 1201.

Figure 29:
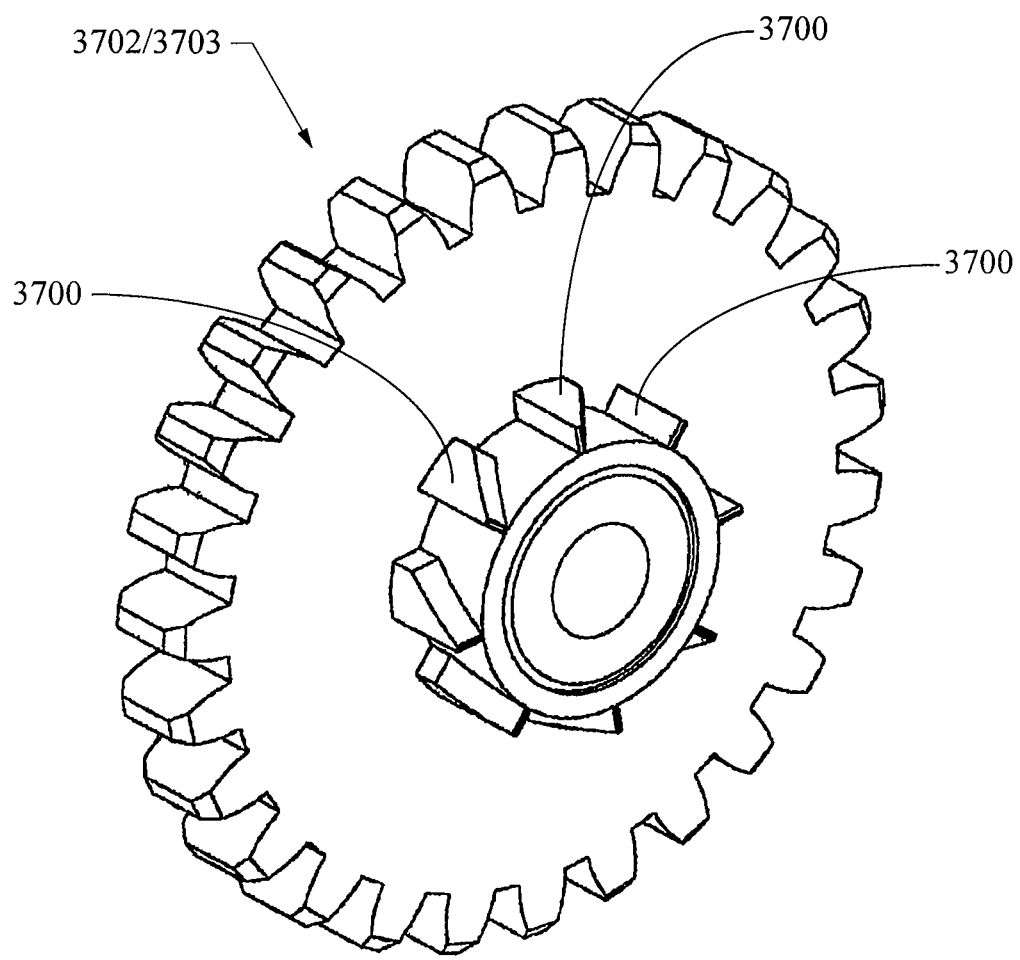
FIG. 29 shows an alternative embodiment of a pulley gear.
Figure 30:
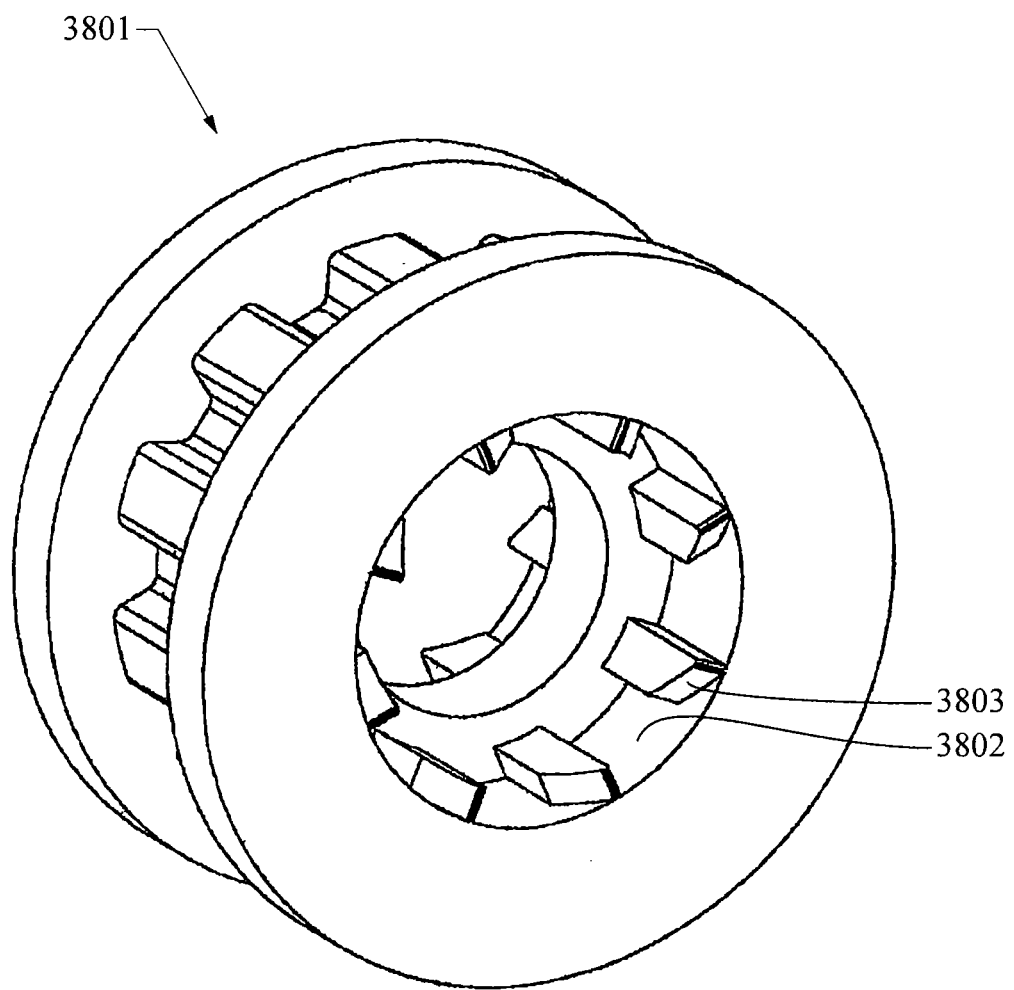
FIG. 30 shows an alternative embodiment of a center drive pulley designed to engage with the pulley gear of FIG. 29.

The first and second pulley gears 503 and 402 may comprise a greater number of ribbed slots 902 compared to that shown in FIG. 9 to facilitate engagement of the pulley gears 503 and 402 with the center drive pulley 901. Alternatively, or in addition, the shape of the ribbed slots 902 of the center drive pulley 901 may be modified to enhance its engagement with the gears 503 and 402. FIG. 29 shows an example of an alternative embodiment of a first and second pulley gear 3702 and 3703 having angled slots 3700. The shape and greater number of slots 3700 may provide improved engagement of the gears 3702 and 3703 with the center drive pulley 3801 shown in FIG. 30. FIG. 30 shows that center drive pulley 3801 contains multiple slots 3802, each of which are defined by adjacently disposed angled structures 3803. The shape of each of the slots 3802 corresponds to the shape of each of the angled slots 3700 (FIG. 29) to allow a secure fit therewithin.

The belt 1201 is shown in FIG. 4 to be wrapped around three pulleys 1211, 1212 and 901. Pulleys 1211 and 1212 may help transfer gear movement into belt movement. Center drive pulley 901 engages with one of the first gear set 500 and the second gear set 400 to cause rotational movement of the belt 1201. Although a three pulley system is shown, more than three pulleys or less than three pulleys are contemplated.

Idlers 1215 and 1216 (FIG. 4) may help to provide wrapping a sufficient amount of the belt 1201 around the center drive pulley 901 for the purpose of preventing belt 1201 slippage from the center drive pulley 901. Referring to FIG. 4, the belt 1201 wraps around idler 1215 and then proceeds down and around the center drive pulley 901. The belt 1201 then proceeds up and around the top of idler 1216. FIG. 4 shows that the idlers 1215, 1216 help the belt 1201 to wrap around more than about 180° of the center drive pulley 901.

The gear mechanism for proximal release of the endoprosthesis 301 (i.e., the inner cannula 1200 moving from the proximal direction to the distal direction as indicated by the arrows in FIG. 33) will now be explained. Reference to the rotational movement of the various gears and pulleys will be made in accordance with perspective views facing the first gear set 500 (FIGS. 2, 4, 8, 11, 12). The directional switch 101 is pushed such that the first pulley gear 503 is engaged with the center drive pulley 901 and the second pulley gear 402 is disengaged from the center drive pulley 901 (FIG. 8). Pulling the trigger 102 in the proximal direction, as indicated by the arrow in FIG. 8, causes the main drive gear 701 to engage with the rack 709 (FIGS. 11 and 12) of the trigger 102 (FIG. 11) and rotate in a clockwise direction (the three arrows in FIG. 12 around first drive gear 502 represent clockwise rotation). Because the main drive gear 701 is directly connected to the drive shaft 702, the drive shaft 702 also rotates in a clockwise direction. As the drive shaft 702 rotates in a clockwise direction, the first drive gear 502 and the second drive gear 401 also rotate in the same direction. The first drive gear 502 is engaged to the first idle gear 501 (shown in FIG. 8), and therefore clockwise rotation of the first drive gear 502 causes the first idle gear 501 to rotate counterclockwise (FIG. 8). The first idle gear 501 is engaged to a first pulley gear 503. Accordingly, counterclockwise rotation of the first idle gear 501 causes the first pulley gear 503 to rotate clockwise (FIGS. 2 and 8). Because the directional switch 101 has been pushed to engage the first pulley 503 with the center drive pulley 901 (FIG. 8), the center drive pulley 901 also rotates in the clockwise direction. With the belt 1201 winding around a center drive pulley 901, two idlers 1215 and 1216 pull in the belt 1201 around the center drive pulley 901, as shown in FIG. 4. The idlers 1215 and 1216 optimize the connection between the belt 1201 and the center drive pulley 901 to minimize slippage of the belt 1201 around the center drive pulley 901. Clockwise rotation of the center drive pulley 901 also causes the belt 1201 to rotate clockwise (FIGS. 2 and 4). The clockwise rotation of the belt 1201 causes the shuttle 1202 and inner cannula 1200 attached thereto to move distally. Because the inner cannula 1200 is connected via the distal tip 1301 to the introducer sheath 1299, distal movement of the inner cannula 1200 causes the distal tip 1301 and the introducer sheath 1299 to also move distally (as shown by the arrows in FIG. 32), thereby enabling proximal release of the endoprosthesis 301.

When the trigger 102 has been deactivated so that the trigger 102 moves distally and returns to its original position (FIGS. 4, 8, 11, and 12), the drive shaft 702 and main drive gear 701 rotate counterclockwise and return to their original position. The drive shaft 702 is permitted to rotate counterclockwise within the one-directional roller clutch bearings 403, 504 (as can clearly be seen in FIG. 8). However, roller clutch bearings 403, 504 prevent the left and right drive gears 401, 502 (as seen in FIG. 8) from rotating counterclockwise upon the trigger 102 being deactivated. Thus, the first and second drive gears 502 and 401 will remain in the position from which they have previously rotated clockwise after activation of the trigger 102. The effect of having the first drive gear and the second drive gears 502 and 401 rotate clockwise but not counterclockwise is that the inner cannula 1200 may continue to be incrementally moved in a distal direction (i.e., proximal release direction) with each successive actuation of the trigger 102. Accordingly, this unidirectional movement of the first and second drive gears 502 and 401 is converted into clockwise rotation of the belt 1201, as seen from the perspective of FIG. 4.

The gear mechanism for resheathing the introducer sheath 1299 in which the introducer sheath 1299 moves from the distal direction to the proximal direction will now be explained. Reference to the rotational movement of the various gears and pulleys will be made in accordance with perspective views facing the second gear set 400 (FIG. 3). The directional switch 101 is pushed such that the second pulley gear 402 is engaged with the center drive pulley 901 and the first pulley gear 503 is disengaged from the center drive pulley 901. Referring to FIG. 3, pulling the trigger 102 in the proximal direction as indicated by the arrow causes the main drive gear 701 to engage with the rack 709 (FIG. 11) of the trigger 102 and rotate in a counterclockwise direction. Because the main drive gear 701 is directly connected to the drive shaft 702, the drive shaft 702 also rotates in a counterclockwise direction. As the drive shaft 702 rotates in a counterclockwise direction, the first drive gear 502 and the second drive gear 401 rotate in the same direction. Because the second drive gear 401 is engaged to the second pulley gear 402, counterclockwise rotation of the second drive gear 401 causes the second pulley gear 402 to rotate clockwise (FIG. 3). The engagement of the second pulley gear 402 with the center drive pulley 901 (as clearly seen in FIGS. 4 and 8) causes the center drive pulley 901 to also rotate in a clockwise direction (FIG. 3). The clockwise rotation of the center drive pulley 901 also causes the belt 1201 to rotate clockwise. The clockwise rotation of the belt 1201 causes the shuttle 1202 and the inner cannula 1200 attached thereto to move proximally. Because the inner cannula 1200 is connected via the distal tip 1301 to the introducer sheath 1299, proximal movement of the inner cannula 1200 causes the distal tip 1301 and the introducer sheath 1299 to also move proximally (as shown by the arrows in FIG. 33), thereby enabling resheathing of the endoprosthesis 301.

The unidirectional movement of the first and second drive gears 502 and 401 is converted into the clockwise rotation of the belt 1201, as seen from the perspective in FIG. 3, and the corresponding proximal movement of the inner cannula 1200 attached thereto. Specifically, when the trigger 102 has been deactivated so that the trigger 102 moves distally and returns to its original position, the drive shaft 702 and main drive gear 701 rotate clockwise with respect to FIG. 3 and return to their original position. The drive shaft 702 is permitted to rotate clockwise within the one-directional roller clutch bearings 403, 504. However, roller clutch bearings 403, 504 prevent the left and right drive gears 401, 502 from rotating upon the trigger 102 being deactivated. The effect of having the first drive gear and the second drive gears 502 and 401 rotate counterclockwise but not clockwise (as shown in FIG. 3) is that the inner catheter 1200 may continue to be incrementally moved in a proximal direction (i.e., resheathing direction) with each successive actuation of the trigger 102.

In order to prevent the self-expanding prostheses 301 from axially moving during axial movement of the introducer sheath 1299, various types of stabilizing elements can be affixed to the prosthesis 301. The stabilizing element maintains the prosthesis 301 in a substantially stationary position by affixing the prosthesis 301 to the inner catheter 1207, as will now be explained.

Figure 18:
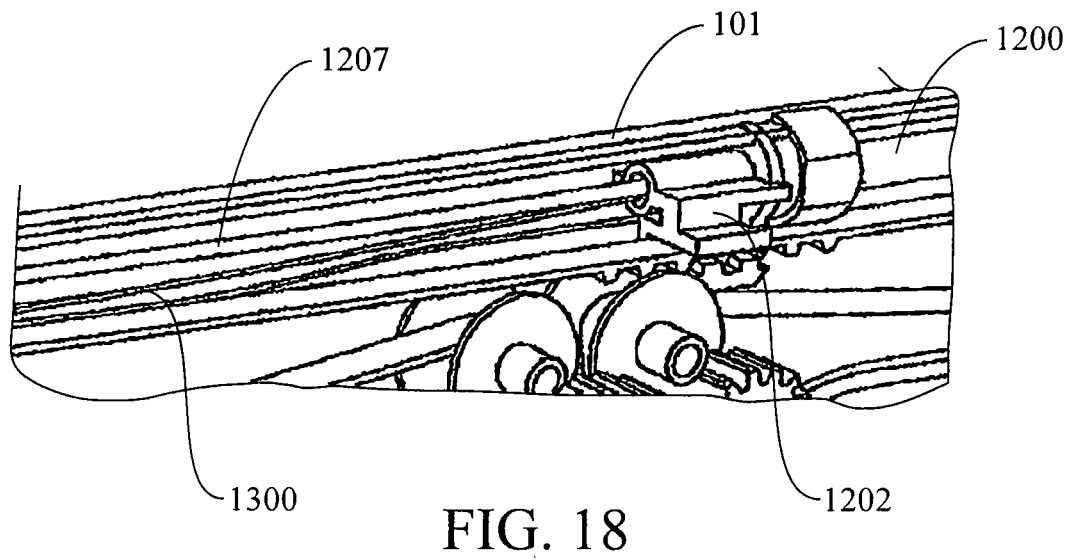
FIG. 18-21 shows an alternative type of stabilizing element for securing the stent to the inner catheter during axial movement of the introducer sheath.
Figure 19:
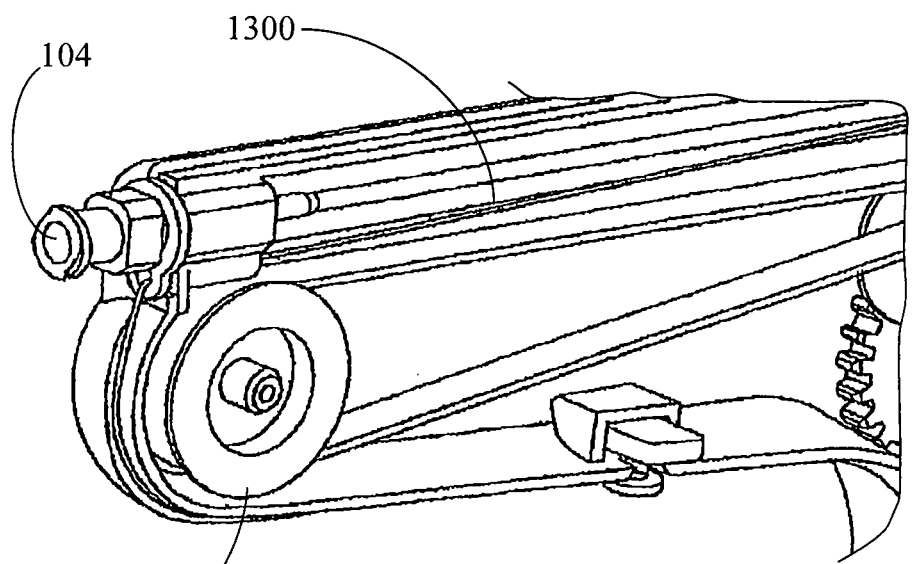
Figure 20:
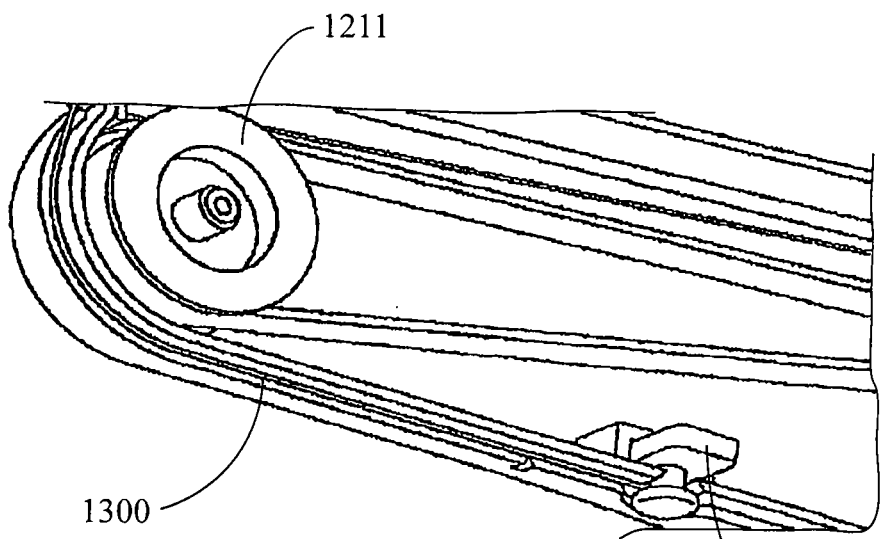
Figure 21:
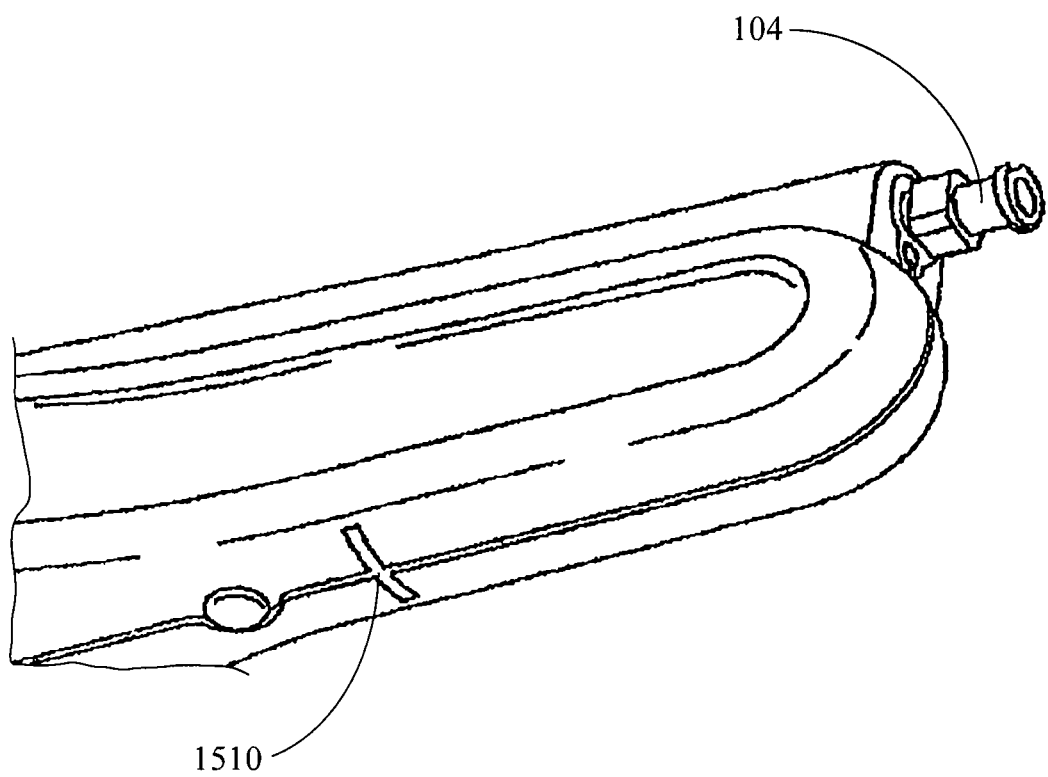

Various types of stabilizing elements are contemplated that will now be described. In one embodiment, the stabilizing element is a suture 1300 which may be configured as shown in FIGS. 18-21. The suture 1300 extends along the handle 111 and thereafter travels towards the endoprosthesis 301 where it may be looped through one or more crowns of the endoprosthesis 301, the crowns being defined by meshed openings of an endoprosthesis 301, which in this embodiment may be a braided stent. Specifically, FIG. 18 shows that the suture 1300 extends through the interior of the shuttle 1202. The suture 1300 extends inside the housing 1101 of the handle 111 of the device 100 and thereafter extends alongside the inner cannula 1200, as shown in FIG. 18. The distal end of the suture 1300 extends from out of the housing 1101 of the handle 111 and towards the endoprosthesis 301. The suture 1300 exits the inner catheter 1207 at the distal end thereof and then may be looped into a retaining collar 1276 (e.g., FIG. 15). Prior to distally travelling towards collar 1276 and being looped therethrough, the suture 1300 may also extend through a crown of the endoprosthesis 301. The looped suture 1300 emerges from the collar 1276 and then may proximally extend through an opening of another crown of an endoprosthesis 301. The suture 1300 then continues to proximally travel along the delivery device until it reaches the rear hub 104 where it exits toward the exterior of the housing 1101 of handle 111, as shown in FIG. 19. After exiting the rear hub 104, the suture 1300 may follow a path where it is connected to the bottom of the device 100 at a post 1500 (FIG. 20). A groove 1510 (FIG. 21) located at the bottom of the device 100 may be used to cut the suture 1300 when the endoprosthesis 301 is ready to be detached from the inner catheter 1207. After the suture 1300 is cut, as shown in FIG. 21, the remainder of the suture 1300 can be pulled through the device 100 by pulling on one end of the suture 1300. Because the suture 1300 is held in place at the one or more crowns of the endoprosthesis 301 and at the post 1500 of the handle 111 (FIG. 20), the endoprosthesis 301 may substantially be held in place to the inner catheter 1207 during axial movement of the introducer sheath 1299.

Figure 13:
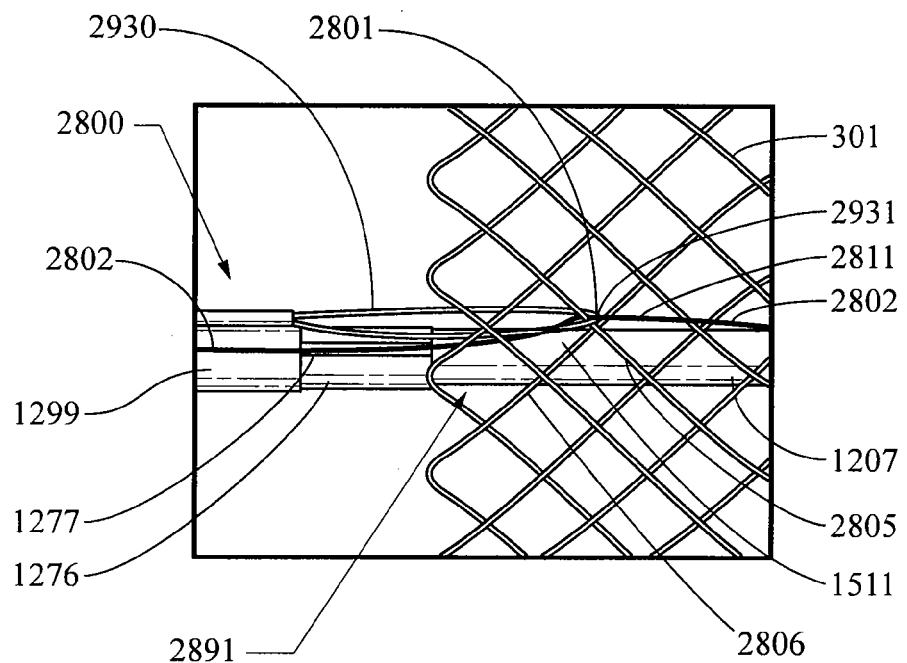
FIG. 13 shows a retaining loop assembly that secures the endoprosthesis to the inner catheter
Figure 14:
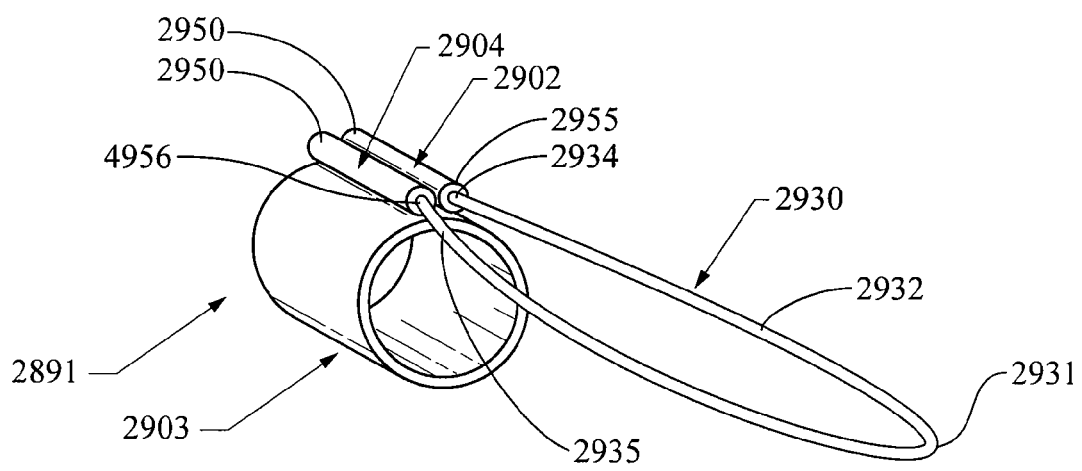
FIG. 14 shows the components of a retaining loop assembly.

FIGS. 13-16 show an alternative embodiment of a stabilizing element used to fixate the distal end of the endoprosthesis 301 to the inner catheter 1207 during axial movement of the introducer sheath 1299 relative to the inner catheter 1207. In this embodiment, the endoprosthesis 301 may also be a braided stent 301 in which the braided elements define meshed openings. The stabilizing element comprises an anchorage assembly 2800 as shown in FIGS. 13 and 14. FIG. 13 shows that the anchorage assembly 2800 includes a retaining loop assembly 2891 and a lockwire 2802. Engagement of the lockwire 2802 with the retaining loop assembly 2891 through a mesh opening of the stent 301 fixates the stent 301 during axial movement of the introducer sheath 1299.

Preventing substantial movement of the lockwire 2802 may assist in fixating the stent 301 during movement of the sheath 1299. In particular, movement of the lockwire 2802 during unsheathing and resheathing relative to the inner catheter 1207 may be further limited by frictional resistance between the lockwire 2802 and the notch 1277 of the retaining collar 1276. The lockwire 2802 may be substantially secured within the notch 1277 by the introducer sheath 1299 that is disposed over the retaining collar 1276. Additionally, the frictional resistance between the sheath 1299 and the lockwire 2802 may be lower than the frictional resistance between the lockwire 2802 and the notch 1277 of the retaining collar 1276 to prevent inadvertent movement of the lockwire 2802 with axial movement of the sheath 1299. The means for imparting a high coefficient of friction to a surface is described in detail in U.S. Pat. No. 5,026,377, which is incorporated by reference herein in its entirety.

The components of the retaining loop assembly 2891 can be more clearly seen in FIG. 14, which does not show that the retaining loop assembly 2891 connected to the inner catheter 1207. The retaining loop assembly 2891, as shown, may include a retaining loop wire 2930, a first pair of cannulas 2902 and 2904, and a second cannula 2903. FIG. 13 shows that the stent 301 is anchored to the inner catheter 1207 by engagement of a lockwire 2802 through the retaining loop wire 2930 and the struts 2805 and 2806 of the stent 301.

Figure 15:
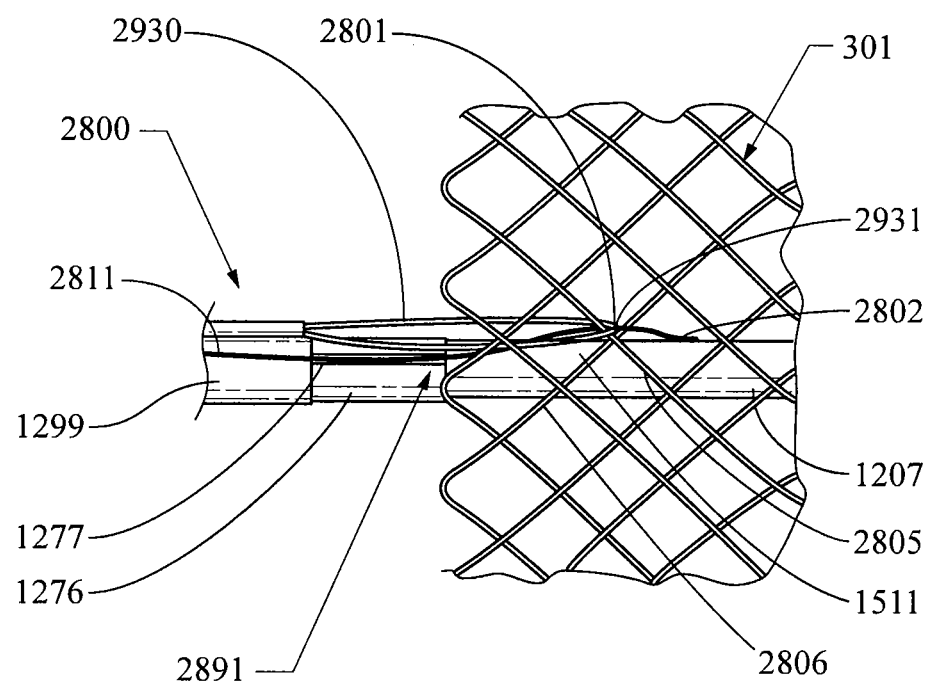
FIG. 15 shows a stent being anchored to the retaining collar of an inner catheter with a retaining loop assembly, the stent not yet completely loaded within the introducer sheath.
Figure 24:
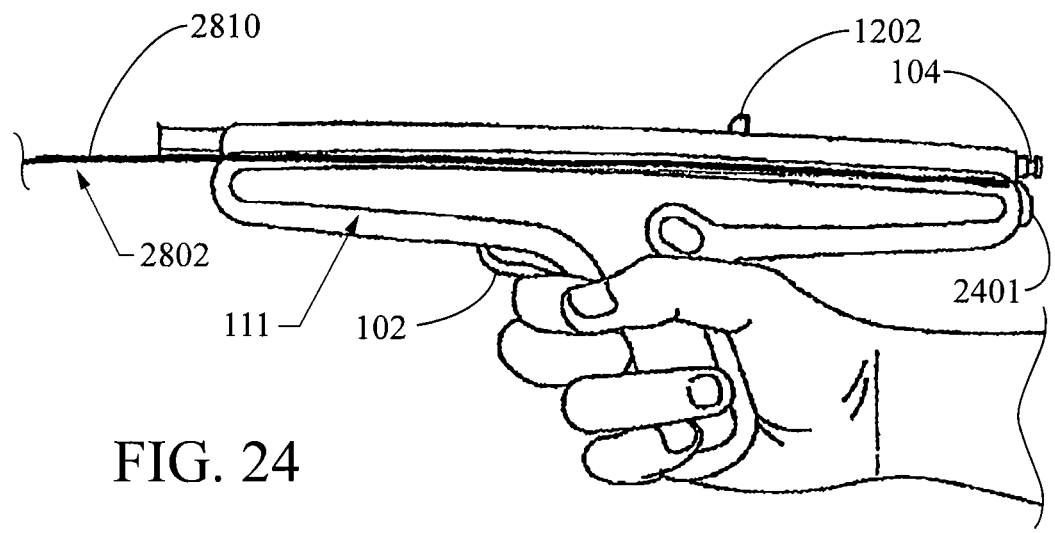

The lockwire 2802 comprises a proximal portion 2810 (FIG. 24) and a distal portion 2811 (FIGS. 13 and 15). FIG. 24 shows that the proximal portion 2810 of the lockwire 2802 extends proximally towards the rear hub 104 of the handle 111 and thereafter terminates as a pigtail 2401 at the rear hub 104. The proximal portion 2810 of the lockwire 2802 may extend alongside inner catheter 1207. Alternatively, the proximal portion 2810 of the lockwire 2802 may extend between inner catheter 1207 and inner cannula 1200 or within inner cannula 1200. FIG. 13 shows that the distal portion 2811 of the lockwire 2802 distally extends along the outside of the stent 301 prior to engaging with the retaining loop assembly 2891 and the stent 301. Note that FIG. 15 illustrates the distal end of the stent 301 being affixed to the distal end of the inner catheter 1207 at a retaining collar 1276, but prior to being completely loaded within the sheath 1299 with the distal portion 2811 of the lockwire 2802. When the distal portion 2811 reaches the apex 2931 of the retaining loop wire 2930, the lockwire 2802 extends into the interior of the retaining loop wire 2930 and then extends through a mesh opening 1511 (FIG. 13) defined by a first strut 2806 and a second strut 2805 of stent 301. The lockwire 2802 travels within the luminal space of the stent 301 and subsequently emerges from the distal end of the stent 301 at which point it extends into a notch 1277 (more clearly seen in FIG. 15) of a retaining collar 1276 located at the distal end of the inner catheter 1207. The notch 1277 is sized to receive the lockwire 2802. The notch 1277 may be coincident with the retaining loop 2930 such that a single longitudinal axis extends between the notch 1277 and the apex of the loop 2930. Such positioning of the loop 2930 relative to the notch 1277 may assist in feeding the lockwire 2802 into the notch 1277 and thereafter between the sheath 1299 and inner catheter 1207. Possible means for affixing the retaining loop assembly 2891 to the inner catheter 1207 include, but is not limited to, soldering or gluing, as shown in FIG. 15.

Having anchored the stent 301 to the inner catheter 1207, the stent 301 may be constrained and loaded within the introducer sheath 1299. The crowns of the stent 301 are collapsed and pushed down to fit within the introducer sheath 1299. The trigger 102 of the device 100 is then pulled to incrementally advance the introducer sheath 1299 over the distal crowns of the stent 301 so as to partially have loaded the distal end of the stent 301 into the proximal end of the introducer sheath 1299. While stent 301 is being loaded, the lockwire 2802 may be pulled proximally to tighten up any excess slack of the lockwire 2802 that may accumulate within the introducer sheath 1299. When the stent 301 has been completely loaded within introducer sheath 1299, the distal portion 2811 of lockwire 2802 will be disposed between the inner catheter 1207 and the introducer sheath 1299. The distal portion 2811 of lockwire 2802 will continue to travel a predetermined distance within the introducer sheath 1299 and eventually terminate as a distal free end (not shown) within the sheath 1299.

Referring to FIG. 13, the point at which the distal portion 2811 of the lockwire 2802, the apex 2931 of the retaining loop wire 2930, and the second strut 2806 of stent 301 intersect each other defines an anchorage point 2801. The stent 301 remains substantially fixated to inner catheter 1207 at anchorage point 2801 during axial movement of the introducer sheath 1299. When the stent 301 is anchored to the inner catheter 1207 at anchorage point 2801 as shown in FIG. 13, resheathing and proximal release of the introducer sheath 1299 over stent 301 is possible. Because the distal portion 2811 of the lockwire 2802 remains in mechanical engagement with the retaining loop assembly 2891, full deployment of the stent 301 into a body lumen in which stent 301 disengages from inner catheter 1207 is not yet possible.

Figure 16:
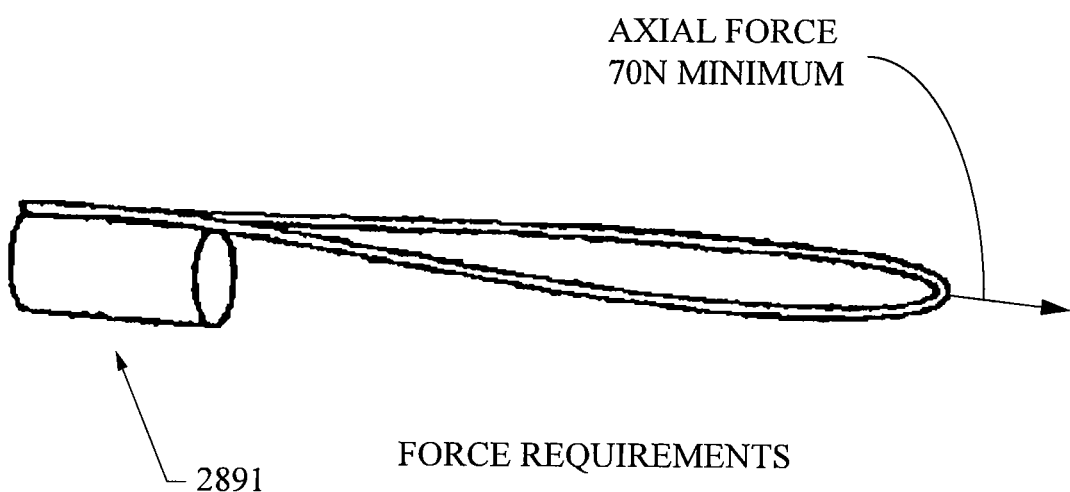
FIG. 16 shows the force generated and imparted to the retaining loop assembly during resheathing.

The force generated and imparted to the retaining loop assembly 2891 during resheathing can rise to about 70 Newtons of axial load during use without breakage, as shown in FIG. 16. Accordingly, it is necessary for the retaining loop assembly 2891 to maintain anchorage of the stent 301 at such relatively high loads. Failure for the retaining loop assembly 2891 to fixate the stent 301 at such high loads may cause the stent 301 to slip along the inner catheter 1207 such that resheathing and/or deployment capabilities are lost. FIG. 14 shows more clearly the components of the retaining loop assembly 2891 which are designed to withstand such loads. The retaining loop wire 2930 is inserted into the first pair of cannulas 2902 and 2904. The first pair of cannulas 2902 and 2904 is shown connected to the second cannula 2903. Numerous means may be used to connect the first pair of cannulas 2902 and 2904 with second cannula 2903. For example, the first pair of cannulas 2902 and 2904 may be connected to the second cannula 2903 by an adhesive. In one embodiment, the first pair of cannulas 2902 and 2904 is laser welded to the second cannula 2903. Other means for joining the cannulas are contemplated, such as, for example soldering. The distal portion 2932 of the retaining loop wire 2930 forms its loop shape. Specifically, the distal portion 2932 of the wire 2930 folds back upon itself to form two proximal sections 2934 and 2935, each of which is shown to extend completely through corresponding openings 2955 and 2956 of the first pair of cannulas 2902 and 2904. The proximal sections 2934 and 2935 of retaining loop wire 2930 are affixed within the inside of corresponding openings 2955 and 2956 of the first pair of cannulas 2902 and 2904 at proximal end 2950, such as, for example, by a spot weld. Because there is no other attachment between proximal sections 2934 and 2935 other than the attachment at proximal end 2950, strain relief of retaining loop wire 2930 occurs which may enable significant flexing of the loop wire 2930 without breakage. In other words, during flexing of the retaining loop wire 2930 as may occur during the loading or the deployment of the endoprosthesis 301, the strain imparted onto the retaining loop wire 2930 may be distributed along the length thereof within the cannula 2902 and 2903.

Additionally, each of the cannulas 2902, 2903, 2904 and the retaining loop wire 2930 may be formed from materials sufficient to enable the retaining loop assembly 2891 to withstand the forces associated with pulling the introducer sheath 1299 over the inner catheter 1207 during the resheathing procedure or proximal release procedure. In one example, each component of the retaining loop assembly 2891 (i.e., the first pair of cannulas 2902 and 2904, the second cannula 2903, and the retaining loop wire 2930) is formed from a metallic alloy, such as, for example, ASTM grade 302 or 304 stainless steel, which can withstand up to about 70 Newtons of axial load without breakage. The tensile strength of the retaining loop wire 2930 is designed to range between 200 to 300 kpsi in order to accommodate for the 70 N load which may be created against retaining loop assembly 2891 by proximal and/or distal movement of the introducer sheath 1299 relative to the inner catheter 1207. The first pair of cannulas 2902, 2904, the second cannula 2903 and the retaining loop wire 2930 may be formed from any other suitable biocompatible material known in the art.

Alternatively, the first pair of cannulas 2902 and 2904 and/or the second cannula 2903 may be formed from a high strength biocompatible polymeric material capable of withstanding the high loads which can occur during resheathing of introducer sheath 1299 and/or full deployment of stent 301 when the introducer sheath 1299 is distally pushed to expose the stent 301. In one embodiment, the first pair of cannulas 2902 and 2904 is formed from polyetheretherketone (PEEK).

Figure 41:
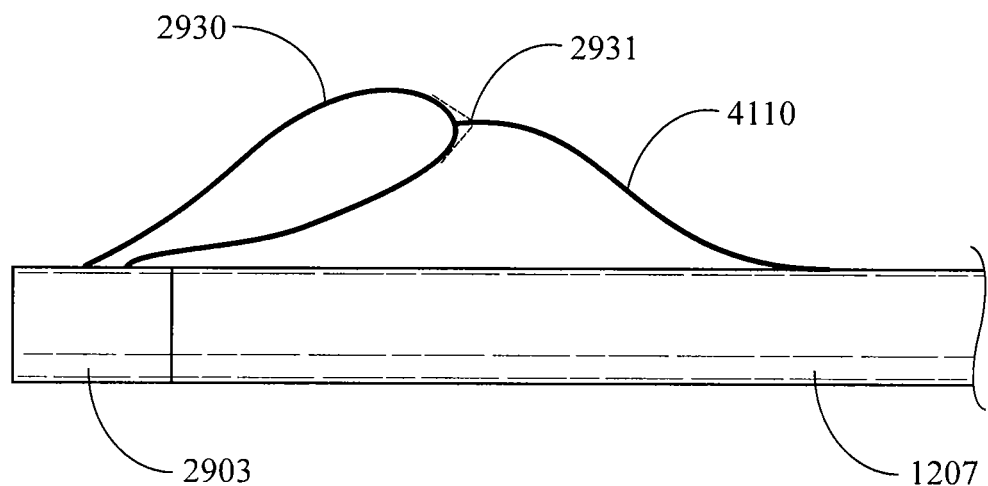
FIG. 41 shows an alternative type of retaining loop design including a stabilizing wire affixed to the retaining loop and the inner cannula.

Variations of the retaining loop design of FIG. 15 are contemplated. In one embodiment, referring to FIG. 15, a stabilizing wire may be attached from the apex 2931 of the retaining loop 2930 to the surface of the inner catheter 1207 to prevent the crowns of the stent 301 from becoming tangled between the cannula 2903 and the retaining loop 2930. FIG. 41 shows the retaining loop 2930 with a stabilizing wire 4110. Stent 301 has been omitted from FIG. 41 for purposes of clarity. One end of the wire 4110 is shown affixed to the apex 2931 of the retaining loop 2930. The other end of the wire 4110 is shown affixed to an outer surface of the inner catheter 1207. Various means for attaching the ends of the wire are contemplated, including spot welding. Accordingly, when sheath 1299 has been withdrawn to cause the stent 301 to radially expand, the stabilizing wire 4110 may prevent retaining loop 2930 from inadvertently hooking onto the stent 301. The wire 4110 may limit significant movement of the retaining loop 2930, thereby allowing the stent 301 to be deployed without interference from the retaining loop 2930.

Figure 37:
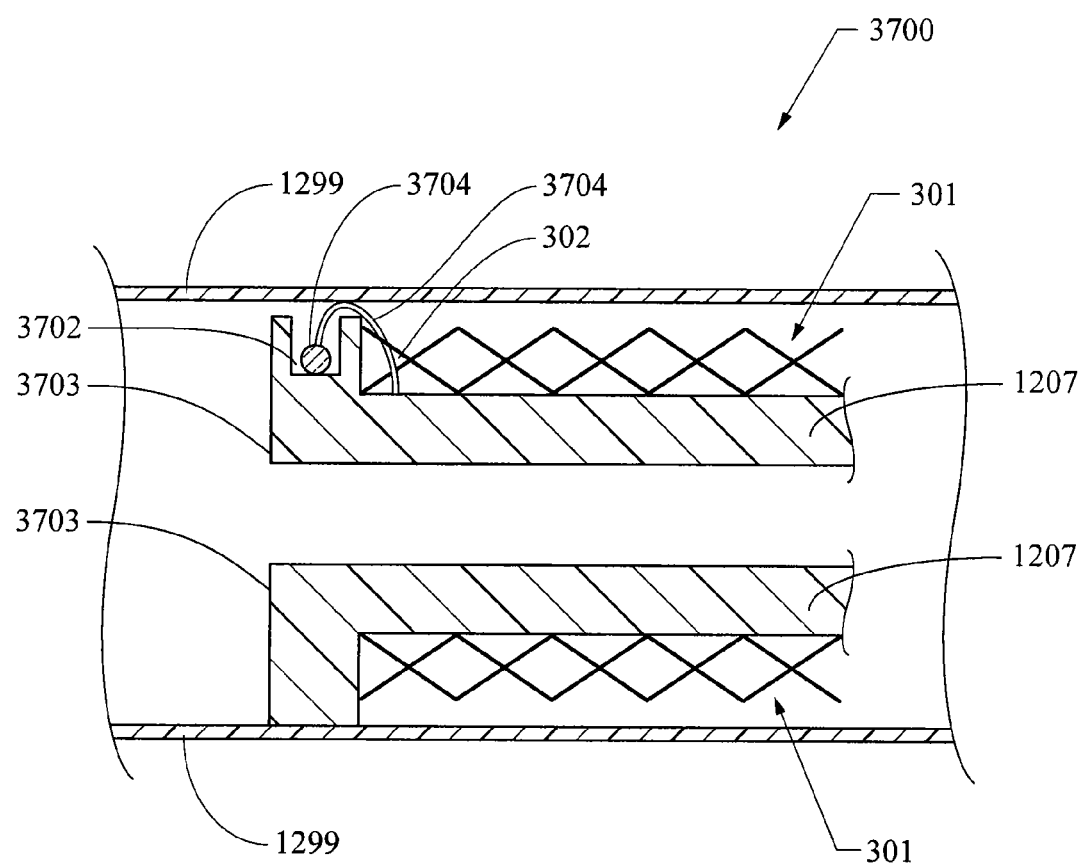
FIG. 37 shows a releasable suture design as an alternative type of stabilizing element for fixating an endoprosthesis to an inner catheter of the delivery device during biaxial movement of an outer sheath.

Other stabilizing elements are contemplated. For example, FIG. 37 shows a releasable suture design 3700 as an alternative type of stabilizing design in which a releasable suture 3701 with a bead 3704 at one of the free ends thereof may be utilized to fixate endoprosthesis 301 to the inner catheter 1207 during biaxial movement of sheath 1299. In particular, FIG. 37 shows that an endoprosthesis 301 is loaded between the inner catheter 1207 and the introducer sheath 1299. A suture 3701 is shown to extend from the inner catheter 1207, through a crown or meshed opening 302 of braided endoprosthesis 301, and into a pocket 3702 of a collar 3703. The portion of the suture 3701 extending into the pocket 3702 may include a beaded element configured to be secured within pocket 3702. In one embodiment, the beaded element may be formed from a glass bead 3704 that is held in position within the pocket 3702 by the introducer sheath 1299. FIG. 37 shows that the glass bead 3704 remains secured within pocket 3702 when the sheath 1299 is disposed over the pocket 3702. Biaxial movement of the introducer sheath 1299 will continue to maintain the glass bead 3704 within the pocket 3702, thereby fixating the endoprosthesis 301 to the inner catheter 1207. When the sheath 1299 has axially moved a sufficient distance to expose the pocket 3702, the bead 3702 will automatically release from the pocket 3702, thereby allowing the endoprosthesis 301 to be disengaged from the inner catheter 1207. Other variations of the releasable suture design 3700 are contemplated, as would be recognized by one of ordinary skill in the art.

Figure 38:
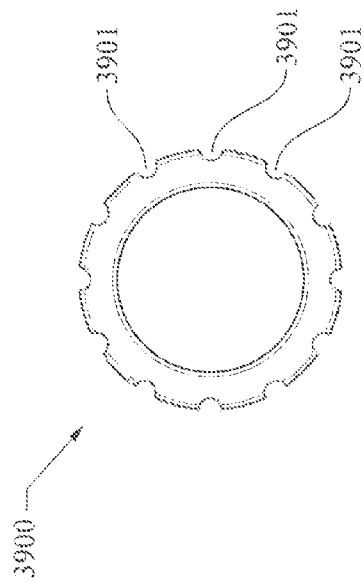
FIG. 38 shows an alternative stabilizing element design including a cannula with multiple stubs affixed to the outer surface thereof for fixating an endoprosthesis to an inner catheter during biaxial movement of an outer sheath.

Still a further alternative design for a stabilizing element is shown in FIG. 38. FIG. 38 shows a solid mechanical lock 3800 having stubs 3802 and 3803 positioned about the outer surface of a cannula 3801. More or less than two stubs may be used depending on the extent to which the stent may be required to be affixed to the inner catheter 1207. Stubs 2802 and 3803 are shown spaced apart by about 180 degrees. The mechanical lock 3800 may be affixed to a distal end of the inner catheter 1207 at approximately the same location where the retaining loop assembly 2891 of FIG. 15 is shown situated along the inner catheter 1207. In one embodiment, the endoprosthesis 301 may be a braided stent which would be mounted at the distal end of the inner catheter 1207. The stubs 2802 and 2803 are sized to engage with the braided stent through the meshed openings thereof. The overlying sheath 1299 compresses the stent onto the stubs 2802 and 2803. When the sheath 1299 has axially moved a sufficient distance to expose the stent 301, the stent 301 will self expand thereby allowing disengagement from the lock 3800 and the inner catheter 1207. Other variations of the mechanical lock 3800 are contemplated, as would be recognized by one of ordinary skill in the art.

Figure 39:
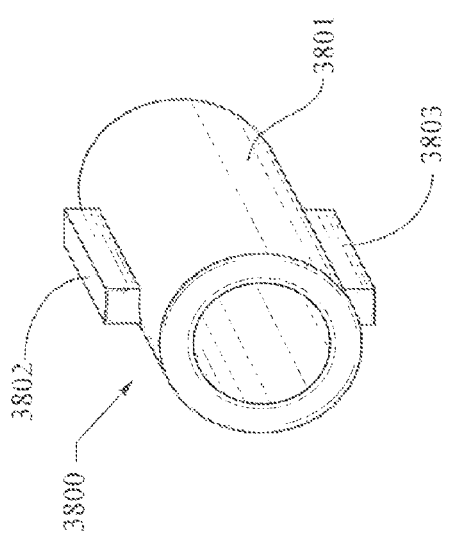
FIG. 39 shows an alternative stabilizing element design with a retaining collar 3900 having a predetermined molded pattern that may used to anchor or affix the endoprosthesis 301 to the inner catheter 1207.

Still further designs are contemplated for anchoring the endoprosthesis 301. FIG. 39 shows a retaining collar 3900 with a predetermined molded pattern that may used to anchor or affix the endoprosthesis 301 to the inner catheter 1207. The molded pattern is shown to include multiple openings 3901 that may correspond to the architecture of the endoprosthesis 301. For example, if the endoprosthesis 301 is a woven stent, the stent is mounted onto the top of the collar 3900 along the molded pattern of the collar 3900 so that openings 3901 contained are sized to receive the wires of the stent 301 such that the stent 301 would insert at least partially therewithin. The retaining collar 3900 may be affixed to a distal end of the inner catheter 1207. The overlying sheath 1299 compresses the wire elements of the stent into the openings 3901. When the sheath 1299 has axially moved a sufficient distance to expose the stent, the stent will self expand, thereby allowing removal of the wire elements of the stent 301 from the openings 3901 of retaining collar 3900 and releasing the stent 301 from the inner catheter 1207. Other variations of the retaining collar 3900 are contemplated, as would be recognized by one of ordinary skill in the art.

Figure 40A:
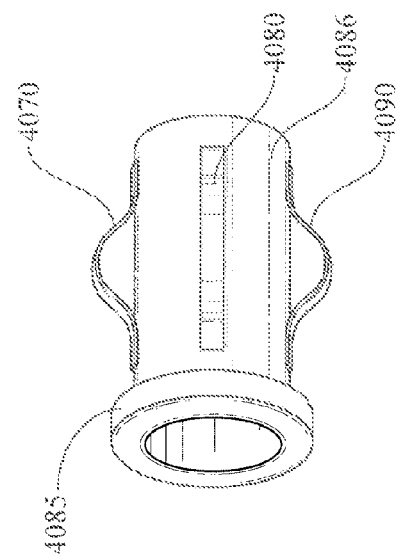
FIG. 40A shows an alternative stabilizing element design including a cannula with multiple hooks welded to an outer surface of the cannula for fixating an endoprosthesis to an inner catheter during biaxial movement of an outer sheath.
Figure 40B:
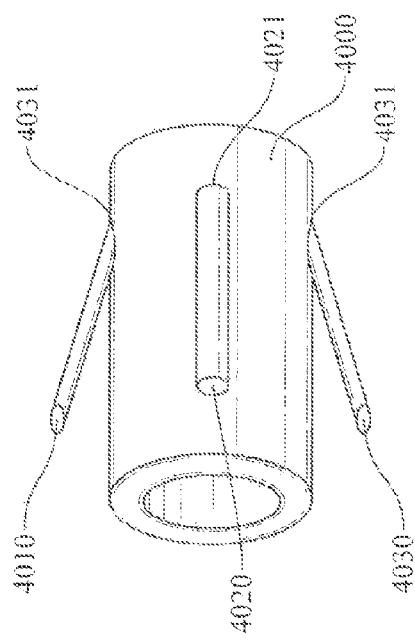
FIG. 40B shows an alternative stabilizing element design including a cannula with multiple spring-loaded hooks welded to an outer surface of the cannula for fixating an endoprosthesis to an inner catheter during biaxial movement of an outer sheath.

FIGS. 40a and 40b each show yet another type of stabilizing element design involving a hook type arrangement. FIG. 40a shows a cannula 4000 comprising hooks 4010, 4020, and 4030, each of which is shown spot welded to an outer surface of the cannula 4000 at corresponding locations 4011, 4021, and 4031. Hooks 4010, 4020, and 4030 are designed to extend through openings of the crowns of a braided stent. The overlying introducer sheath 1299 maintains adequate compression on the stent and hooks 4010, 4020, and 4030 so as to enable hooks 4010, 4020, and 4030 to interlock with stent 301 by extending through the crowns or meshed openings along a distal end of the stent. The cannula 4000 may be affixed to a distal end of the inner catheter 1207. When the introducer sheath 1299 has axially moved a sufficient distance to expose the hooks 4010, 4020, and 4030, the hooks 4010, 4020, and 4030 will revert to its biased configuration, as shown in FIG. 40a. With the hooks 4010, 4020, and 4030 moved outwards, the stent 301 may be disengaged from the cannula 4000 and the inner catheter 1207. Other variations of the cannula 4000 are contemplated, as would be recognized by one of ordinary skill in the art. For example, more or less than three hooks may be used to secure stent 301 to the cannula 4000. Other means for securing the hooks to the cannula 4000 are contemplated in addition to spot welding.

Other hook designs are also contemplated, as shown in FIG. 40b. FIG. 40b shows another variation of the hook-type arrangement in which hooks 4070, 4080, and 4090 are spring-loaded and designed to loop through crowns along the distal end of the stent. Specifically, one end of each of the hooks is affixed to a retaining collar 4085 and the other end of each of the hooks 4070, 4080, and 4090 is shown spot welded to an outer surface of a cannula 4086. It should be understood that various types of hook type arrangements are contemplated.

Figure 42:
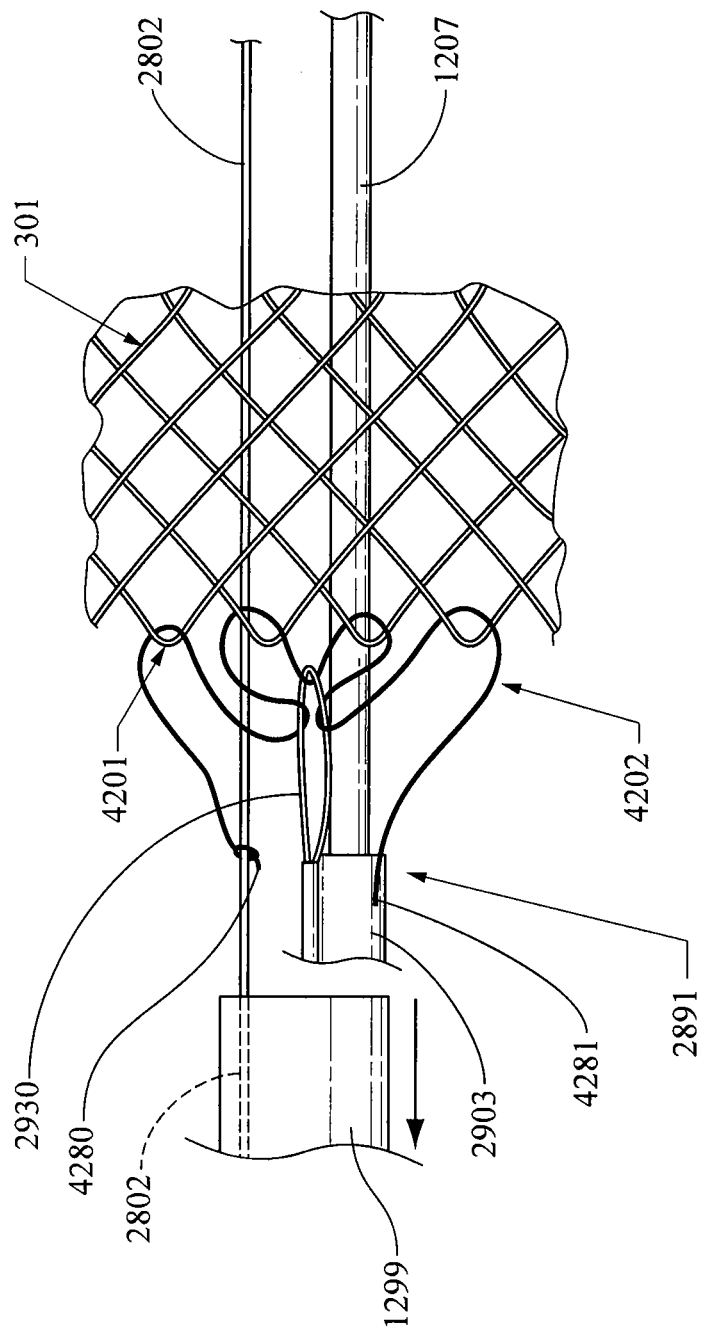
FIG. 42 shows an alternative stabilizing structure for affixing an endoprosthesis to an inner catheter of the delivery device.

In addition to the above described stabilization elements which may be characterized as automatically releasing from an endoprosthesis upon removal of the overlying introducer sheath 1299, other stabilization elements are contemplated which maintain engagement with the endoprosthesis even though sheath 1299 has been slidably withdrawn from the endoprosthesis and the stabilization element. FIG. 42 shows an example of such a stabilization element. Suture 4202 is shown connected between the retaining loop assembly 2891 and the crowns 4201 of the stent 301. One free end 4281 of the suture 4202 may be bonded to the cannula 2903, as shown in FIG. 42. Another free end 4280 of the suture 4202 may be knotted to the lockwire 2802, as also shown in FIG. 42. Retaining loopwire 2930 loops through the suture 4202 at various locations. Introducer sheath 1299 has been distally moved a sufficient amount relative to inner catheter 1207 (as indicated by the arrow) to entirely expose the retaining loop assembly 2891 and the stent 301. As result, stent 301 is fully radially expanded. The stent 301 remains secured to the inner catheter 1207 so long as the stent 301 remains secured to the suture 4202. Accordingly, this embodiment of FIG. 42 enables the stent 301 to be distally pushed. Specifically, as the device 100 moves distally, the cannula 2903 also moves distally. As a result, the retaining loopwire 2930 pulls on portions of the suture 4202 that are looped through the crowns 4201 of the stent 301. These looped portions of the suture 4202 subsequently pull directly on the crowns 4201 to cause the distal end of the stent 301 to collapse. The reduction in diameter at the distal end of the stent 301 enables the stent 301 to be moved to a different target area. Such a capability allows a user to reposition the stent 301 distally even after the sheath 1299 has been slidably withdrawn and the stent 301 has fully expanded.

When the stent 301 is ready to be detached from the retaining loop assembly 2891, a proximal end (not shown) of the suture 4202 is grasped causing the knot between suture end 4280 and the lockwire 2802 to loosen. The end 4281 of the suture 4202 remains bonded to an outer surface of the cannula 2903. Upon loosening of the knot, the suture 4202 begins to unravel from the crowns 4201, eventually causing the stent 301 to be fully detached from device 100 and deployed at a target site. The delivery device 100 is then withdrawn from the target site with suture 4202.

Various other structural members may be used besides the retaining loop assembly 2891 of FIG. 42. As an example, a bilumen tubing may be used in combination with the suture loop 4202 to secure the stent 301 to the inner catheter 1207. A lockwire 2802 extends through one of the lumens of the bilumen tubing, which would be affixed along a distal end of the inner catheter 1207. In one embodiment, a section of the bilumen tubing is cut away so as to allow the end 4280 of the suture 4202 to secure (e.g., knotted or wrapped) to the lockwire 2802. The other end 4281 of the suture 4202 emerges from within the exposed section of the bilumen tubing and weaves in a pattern similar to that shown in FIG. 42 through the crowns 4201 of the stent 301. As the bi lumen tubing is proximally pulled and removed from the target site, the lockwire 2802 contained therewithin pulls on the end 4280 of suture 4202, thereby causing the suture 4202 to pull on the crowns 4201 of the stent 301. Eventually the knot loosens. As the knot loosens, the suture 4202 unravels and disengages from the crowns 4201 of the stent 301.

Figure 28:
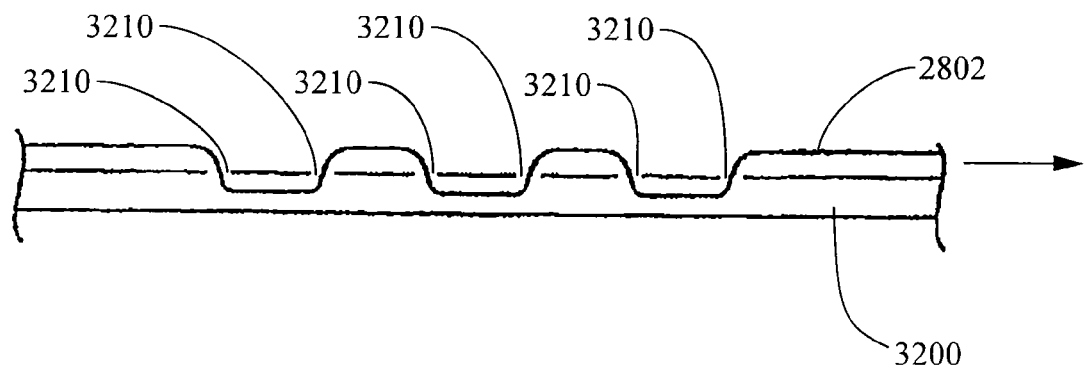
FIG. 28 shows a frictional mechanism for preventing premature disengagement of a lockwire from a stent.

The proximal release device 100 may be used to deploy other endoprostheses, in addition to an esophageal stent. For example, enteral or colonic stents may also be deployed using the device 100. The lockwire 2802 for deployment of an enteral or colonic stent may be routed through the delivery device 100 so as to avoid contact with the movable introducer sheath 1299, thereby preventing inadvertent movement of the lockwire 2802 with the sheath 1299. Alternatively, inadvertent movement of the lockwire 2802 with sheath 1299 may be achieved by frictionally engaging the lockwire 2802 with a frictional member so that the frictional resistance between the lockwire 2802 and the member is greater than that between the lockwire and the sheath 1299. Various frictional engagements between lockwire 2802 and the member may be used. FIG. 28 shows one example of such a member in which a frictional mechanism is incorporated into the proximal delivery device 100 to prevent premature disengagement of the lockwire 2802 with the retaining loop wire 2930 at the anchorage point 2801 (FIG. 13) when the sheath 1299 proximally moves. FIG. 28 shows a static tube 3200 that may serve as the frictional mechanism. The static tube 3200 may be disposed at the distal end of the handle 111 of device 100 (FIG. 1) and coaxially between inner catheter 1207 and inner cannula 1200. FIG. 28 shows a side profile of an exemplary static tube 3200. The static tube 3200 has a predetermined longitudinal length. Any means may be used to affix the static tube 3200 between inner catheter 1207 and inner cannula 1200, including, for example, an adhesive or a mechanical connector. A predetermined number of slits 3210 are created within the wall of static tube 3200 into which the lockwire 2802 loops or weaves in and out. This weaving of the lockwire 2802 increases the frictional force required for pulling the lockwire 2802 out from the slits 3210 of static tube 3200. Generally speaking, increasing the number of slits 3210 and increasing the longitudinal length of static tube 3200 along which the slits 3200 span therealong will tend to increase the frictional force required to completely pull lockwire 2802 out of static tube 3200. Accordingly, the static tube 3200 may substantially prevent the lockwire 2802 from inadvertently slipping proximally or distally between the inner catheter 1207 and the inner cannula 1200. In other words, the lockwire 2802 remains stationary at the anchorage point 2801 until it is intended to be proximally pulled therefrom so that premature release of the stent 301 by the lockwire 2802 is prevented. Such a frictional mechanism may be conducive when delivery and deployment of the stent 301 is occurring within tortuous body pathways.

Disengagement of the lockwire 2802 occurs when the stent 301 is ready to be fully deployed at a target site within a body lumen. Directional switch 101 (FIG. 1) is pressed to actuate the first gear set 500 (FIG. 2) to enable distal advancement of the introducer sheath 1299 relative to the inner catheter 1207. With the first pulley gear 503 mechanically coupled to the center drive pulley 901 (FIG. 4), trigger 102 is actuated multiple times to advance the introducer sheath 1299 in the distal direction relative to the inner catheter 1207 until the stent 301 has fully radially expanded. The introducer sheath 1299 is distally advanced so as to fully expose the self-expandable stent 301 from the proximal end of the stent 301. During stent 301 deployment, the lockwire 2802 is disengaged from the strut 2806 of stent 301 and from retaining loop wire 2930 (FIG. 13). FIG. 24 shows that the lockwire 2802 extends proximally and terminates as a pigtail 2401 at the rear hub 104 of the handle 111 of the device 100. The pigtail 2401 is pulled so as to remove lockwire 2802 in a proximal direction from anchorage point 2801. The lockwire 2802 is completely removed from the device 100, thereby disengaging the stent 301 from inner catheter 1207. At this juncture, the stent 301 is completely deployed within the body lumen. The stabilization embodiments described above in conjunction with FIGS. 13-16 and FIG. 28 may provide many advantages. The retaining loop assembly 2891 does not substantially increase the lateral profile of outer catheter 1200 and inner catheter 1207, thereby enabling through the scope (TTS) self-expandable stents, such as duodenal and colonic stents, to be advanced through an endoscopic accessory channel, which typically has a diameter of about 3.7 mm or less. Additionally, the retaining loop assembly 2891 is designed and constructed to withstand the large axial loads (FIG. 16), which can be incurred during resheathing or complete deployment of stent 301, without breakage of retaining loop wire 2930 or detachment of second cannula 2903 from inner catheter 1207 (FIG. 15). Incorporation of the static tube 3200 described above may also prevent premature disengagement of the stabilization elements. Particularly, the static tube 3200 enables lockwire 2802 to remain stationary at the anchorage point 2801 to fixate the stent 301 to inner catheter 1207 until the stent 301 is intended to be fully deployed and therefore disengaged from inner catheter 1207.

Figure 22:
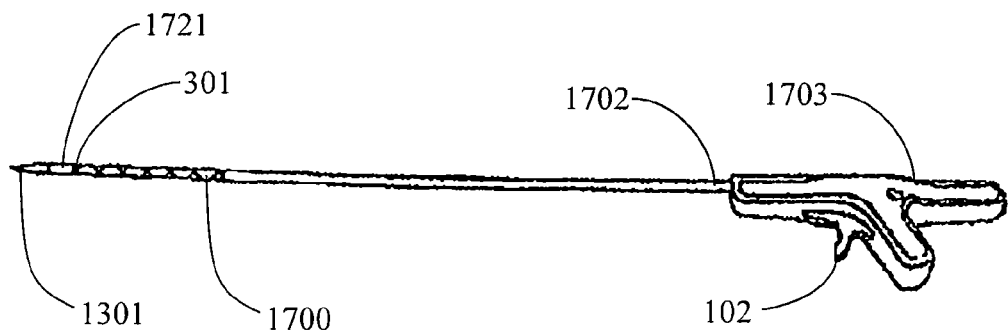
FIG. 22 shows the entire delivery device preloaded with a stent at the distal tip of the delivery section.

Having described the structure of the device 100 and the operation of the device 100 (i.e., the internal gear mechanism to distally advance or proximally resheath the introducer sheath 1200) and the various stabilization elements that may be utilized to fixate the stent during the resheathing process, a method of use of the device 100 may now be described. The device 100 may be used to deploy various prostheses. As an example, a method of deploying an esophageal stent 301 will now be described. The esophageal stent 301 is loaded in between the inner catheter 1207 and the outer sheath 1299 along the distal region 1700 of the device 100, as shown in FIG. 22. Part of the loading process of the stent 301 involves feeding locking wire 2802 through one of the mesh openings 1511 at the distal end of the stent 301 to affix the stent 301 to the distal end of the inner catheter 1207 at a retaining collar 1276, as was described and shown in FIGS. 13 and 15.

Figure 23:
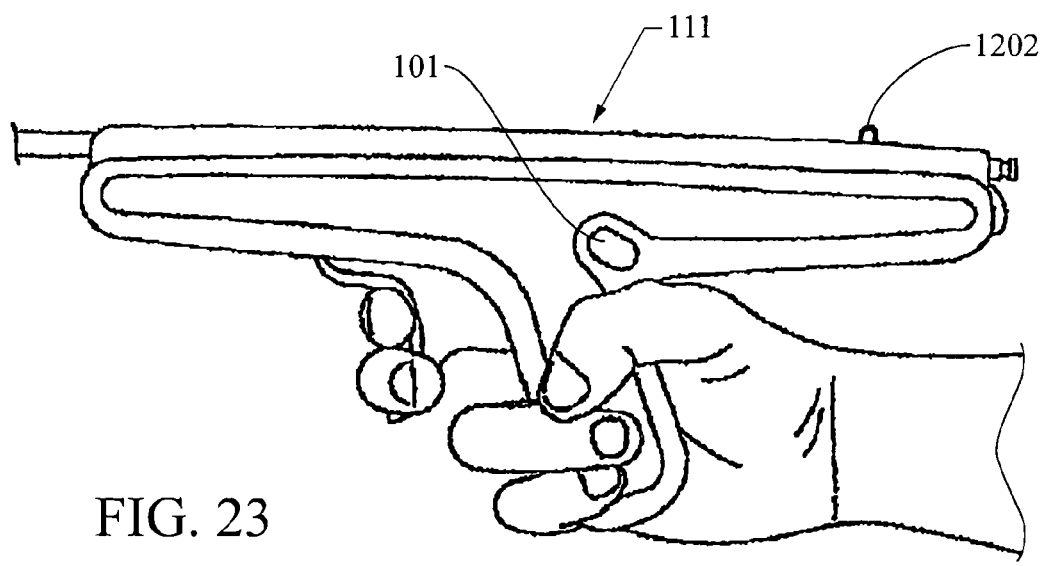
FIGS. 23-26 show a method of use of the delivery device.
Figure 25:
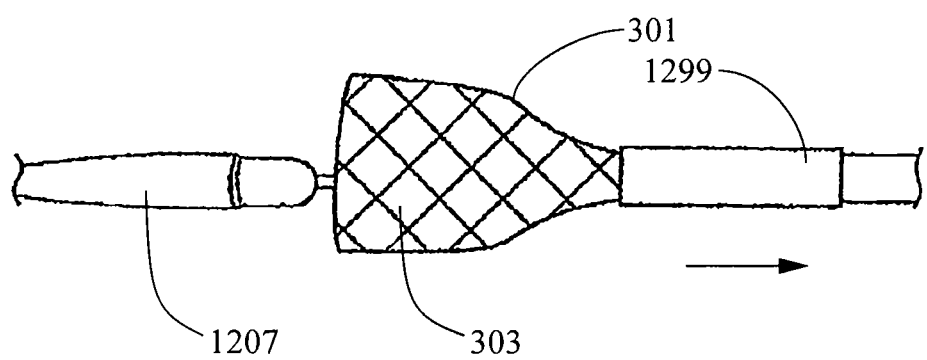
Figure 26:
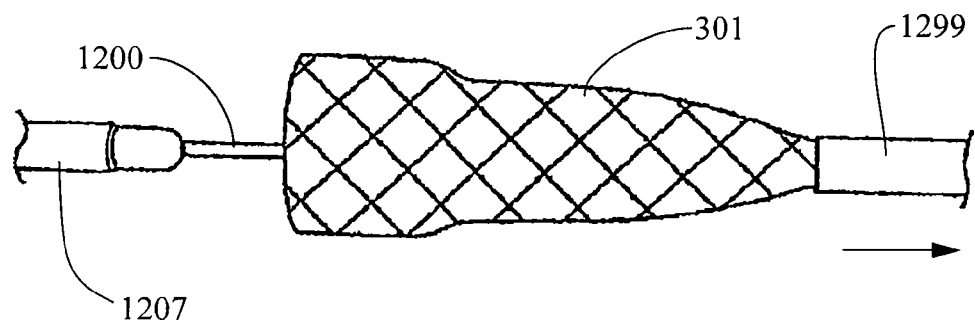
Figure 27:
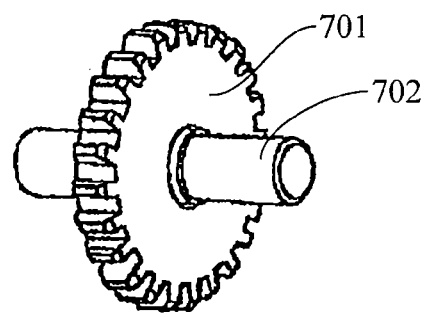
FIG. 27 shows a main drive gear rotationally fixed to the drive shaft.

Having loaded the esophageal stent 301 and affixed the locking wire 2802 to the esophageal stent 301, the delivery and deployment process may begin. The delivery device 100 comprises a stent delivery section 1702 and an external manipulation section 1703. The delivery section 1702 travels through the body lumen during the procedure and delivers the prosthesis to a desired deployment site within the esophagus. The external manipulation section 1703 includes handle 111 which remains outside of the body during the procedure. The external manipulation section 1703 includes trigger 102 and can be manipulated by the physician with a single hand (FIG. 23) to position and release the stent 301 into the body lumen. After having delivered the delivery section 1702 of the delivery device 100 to the target site within the esophagus, the deployment of the stent 301 may begin. The physician presses the directional switch 101 to actuate the first gear set 500 (FIG. 2) to enable distal advancement of the introducer sheath 1299 relative to the inner catheter 1207. FIG. 23 indicates that the shuttle 1202 is positioned near the proximal end of the housing 1101 of the handle 111. Having pressed the directional switch 101 to actuate the first gear set 500 with the center drive pulley 901, the physician may grasp the trigger 102 of the device 100 with a single hand, as shown in FIG. 23, to actuate the trigger 102 for the first time. The other hand may be free to perform other tasks. FIG. 24 indicates that the trigger 102 has been completely pulled in the proximal direction. In particular, the tip of the shuttle 1202 has distally moved after one actuation of the trigger 102. With the second pulley gear 402 still mechanically coupled to the center drive pulley 901, trigger 102 is actuated multiple times to distally advance the introducer sheath 1200 in the proximal direction relative to the inner catheter 1207 until a portion of the esophageal stent 301 has become exposed and partially radially expanded, as shown in FIGS. 25 and 26. Further actuations of the trigger 102 cause the introducer sheath 1299 to distally advance even further, thereby exposing an increasing portion of the proximal portion 303 of self-expanding stent 301, as shown in FIG. 26. Distal movement of the sheath 1299 during unsheathing of the stent 301 will not cause lockwire 2802 to also move distally therewith because the lockwire 2802 is fixably connected at its proximal end as a pigtail to the rear hub 104 of the handle 111 (FIG. 24). As a result, the stent 301 remains fixated to retaining loop assembly 2800 and the inner catheter 1207.

At this juncture, notwithstanding partial proximal release and radial expansion of the stent 301 as shown in FIG. 25, the device 100 may be activated to resheath the introducer sheath 1299 over the stent 301 to allow repositioning of the stent 301 within the esophagus. The physician may need to resheath and reposition the stent 301 as a result of, for example, having placed the stent 301 in an incorrect position. The directional switch 101 may be pressed to disengage the center drive pulley from the first pulley gear and to engage the center drive pulley with the second pulley gear 402 (FIG. 8). Having activated the second gear set 400 with the center drive pulley 901, actuation of the trigger 102 one or more times enables the introducer sheath 1299 to move proximally and resheath over the stent 301 until the stent 301 is fully constrained back within the sheath 1299 (FIG. 33). The retaining loop cannula assembly 2800 or any of the other stabilization elements described in FIGS. 37-42 will prevent stent 301 from having a tendency to proximally move with sheath 1299 as result of the friction therebetween.

With the stent 301 fully recaptured within the introducer sheath 1299, the external manipulation section 1703 may be maneuvered to reposition the delivery section 1702 within the body lumen. After repositioning the delivery section 1702, the directional switch 101 may be reconfigured to reactivate the first gear set 500 with the center drive pulley 901 such that distal advancement of the sheath 1299 occurs, thereby exposing the stent 301 from a proximal end thereof. The lockwire 2802 and retaining loop assembly 2800 retains the stent 301 and prevents it from axially moving with axial movement of sheath 1299.

Figure 17:
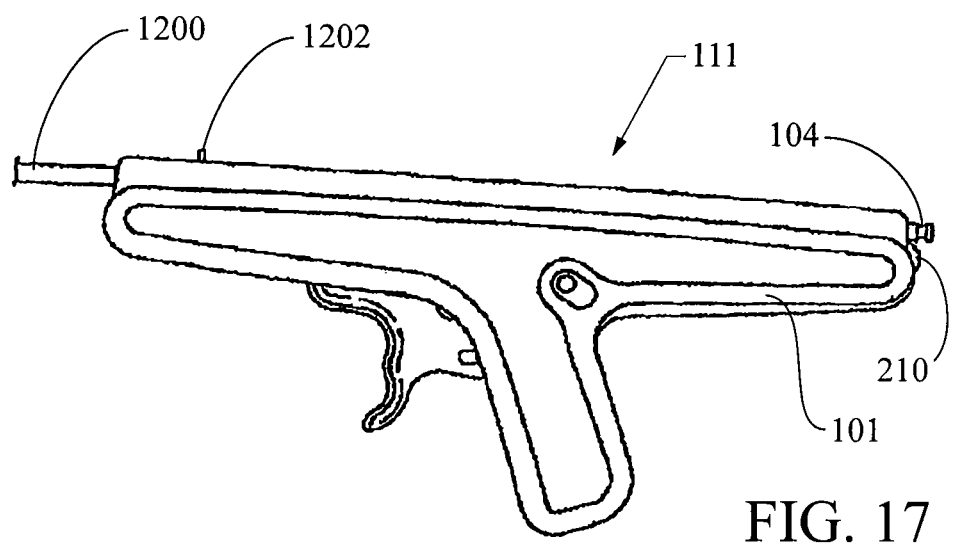
FIG. 17 is a perspective view of a handle portion of the delivery device.

Referring to FIG. 22, during deployment, the distal region 1700 of the device 100 along the introducer sheath 1299 may comprise a transparent or translucent material to enable the physician to visually observe the stent 301 and how it is positioned in relation to the esophageal stricture. FIG. 17 shows that the top-most portion of the shuttle 1202 protrudes through the housing 1101 of the handle 111. The top-most portion of the shuttle 1202, as shown in FIG. 17, distally moves as the introducer sheath 1299 is distally advanced relative to the inner catheter 1207 and may be used as a visual indicator to determine when resheathing capabilities have been lost. The distance that the top-most portion of the shuttle 1202 distally moves may correspond to the distance that the introducer sheath 1299 has distally advanced. The top-most portion of the shuttle 1202 can distally move a predetermined threshold distance beyond which the physician will realize that the introducer sheath 1299 cannot be distally advanced any further without losing the ability to resheath and recapture the stent 301 within the introducer sheath 1299. Alternatively, the point at which the top-most portion of the shuttle 1202 aligns with a predetermined visual marker on the outer housing 1101 of the handle 101 can also indicate the loss of the ability to resheath.

In an alternative embodiment, one or more radiopaque markers 1721 (FIG. 22) may be used under fluoroscopy to determine the distance that the introducer sheath 1299 has axially moved in either the proximal or distal direction. The one or more radiopaque markers 1721 may be placed on the introducer sheath 1299 adjacent to the distal tip 1301, as shown in FIG. 22. The one or more markers 1721 may be utilized to determine when the resheathing capabilities have been lost. For example, as the introducer sheath 1299 is distally advanced with the one or more radiopaque markers 1721 affixed thereto, a radiopaque marker on the inner catheter 1207 may be positioned such that if the marker 1721 on introducer sheath 1299 aligns with the marker 1721 on the inner catheter 1207, the physician will be able to determine that the stent 301 cannot be proximally released any further without losing the ability to resheath and recapture the stent 301 within the introducer sheath 1299.

As can be seen, the device 100 is capable of incrementally deploying the stent 301 in a proximal release manner. In the above examples described, one full actuation of the trigger 102 may distally move the belt 1201 and hence the sheath 1299 from about 5 mm to about 10 mm. Such incremental deployment may facilitate greater accuracy in positioning of the stent 301 at the target region. On the contrary, a conventional push-pull delivery device has less control as compared to the delivery device 100 because the conventional push-pull delivery device cannot withdraw the outer sheath in such small, precise increments. Conventional push-pull delivery devices typically require the user to maintain one portion of the handle 111 in a fixed position and manually either pull in a proximal direction relative to the fixed portion of the handle 111 or push in a distal direction relative to the fixed portion of the handle 111 to resheath the stent. The speed and control of the pulling and pushing of such conventional push-pull delivery devices is entirely dependent on the user, thereby preventing deployment in the small, precise increments which device 100 can perform. Additionally, stents with low or high deployment forces may contribute to the lack of control of push-pull delivery devices. The lack of control may result in sudden proximal movement of the outer sheath of about 50 mm or more, resulting in inaccurate placement of the deployed stent.

Another advantage of the device 100 as has been described is the ability to resheath the introducer sheath 1299 over the stent 301. The resheathing feature gives the physician the ability to make real-time adjustments during the deployment procedure such that the stent 301 may be repositioned. In the examples described, the stent 301 may be resheathed even after about 10% of the stent 301 has been proximally released or as much as about 95% of the stent 301 has been proximally released. Yet other advantages include the ability to use a single hand to deploy the stent 301. The other hand may be free to perform other tasks, such as holding an endoscope when deploying a self-expandable stent therethrough. It should be understood that the above described deployment and resheathing methods may also be utilized for TTS stents such as colonic or duodenal stents.

Yet still a further advantage of the proximal release device 100 is the ability to view the proximal side of the endoprosthesis directly when deployed with an endoscope that is placed parallel to the endoprosthesis. Such visualization allows real-time monitoring at the proximal side of the endoprosthesis relative to the stricture and the anatomy.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. Furthermore, the advantages described above are not necessarily the only advantages of the invention, and it is not necessarily expected that all of the described advantages will be achieved with every embodiment of the invention.

The invention claimed is:

1. A device for deploying an intraluminal device, comprising:
   a gear mechanism comprising a first gear set, a second gear set, a drive shaft, and a main drive gear affixed to the drive shaft, the first gear set comprising a first drive gear, the second gear set comprising a second drive gear, wherein the first drive gear and the second drive gear are drivingly coupled to the drive shaft via one-directional roller clutch bearings, the one-directional roller clutch bearings configured to drive the first and second drive gear when the drive shaft is rotated in one of clockwise and counter-clockwise directions;
   a trigger comprising a rack engaging the main drive gear, the trigger being reciprocally movable to rotationally drive the main drive gear and the drive shaft;
   a drive pulley adapted to be alternatively mechanically coupled to one of the first gear set and the second gear set;
   an introducer sheath operably connected to the drive pulley; and
   an expandable prosthesis constrained within the introducer sheath,
   wherein the sheath is movable in a distal direction relative to the prosthesis when the drive pulley is mechanically coupled to the first gear set so as to release the prosthesis from a proximal end thereof, and further wherein the sheath is retractable in a proximal direction relative to the prosthesis when the drive pulley is mechanically coupled to the second gear set so as to resheath over the prosthesis.

2. The device of claim 1, further comprising an inner elongate member, wherein the prosthesis is disposed over the inner elongate member along a distal portion thereof.

3. The device of claim 2, further comprising a belt coupled to the drive pulley, the belt being disposed within a housing of the device.

4. The device of claim 3, wherein the belt rotates in a first direction when the drive pulley is mechanically coupled to the first gear set, and further wherein the belt rotates in a second direction when the drive pulley is mechanically coupled to the second gear set.

5. The device of claim 3, further comprising an inner cannula extending within the inner elongate member, the inner cannula having a proximal end mechanically coupled to the belt and a distal end operably connected to the introducer sheath.

6. The device of claim 2, further comprising a means for securing the prosthesis to the inner elongate member during axial movement of the sheath.

7. The device of claim 6, wherein the means for securing the prosthesis to the inner elongate member is configured to distally reposition the prosthesis after being expanded.

8. The device of claim 4, wherein the sheath releases a proximal portion of the prosthesis from within the sheath when the belt rotates in the first direction, and further wherein the sheath resheaths over the prosthesis when the belt rotates in the second direction.

9. The device of claim 1, further comprising an atraumatic sheath overlying the introducer sheath.

10. The device of claim 1, wherein the introducer sheath further comprises an inner cannula, the inner cannula extending through a lumen of the inner elongate member and terminating as a distal tip of the device.

11. A device for delivering an intraluminal device, comprising:
    a housing comprising:
    a gear and pulley mechanism comprising a first gear set and a second gear set, the first gear set and the second gear sets each being coupled to a drive shaft via on-directional roller clutch bearings, the one-directional roller clutch bearings configured to drive the first gear set when the drive shaft is rotated in one of the clockwise and counter-clockwise directions, and further configured to drive the second gear set when the drive shaft is rotated in the other of the clockwise and counter-clockwise directions;
    a trigger comprising a rack engaging the main drive gear, the trigger being reciprocally movable to rotationally drive the drive shaft; and
    a drive pulley adapted to be alternatively mechanically coupled to one of the first gear set and the second gear set,
    an elongate member fixably connected to a distal end of the housing; an expandable prosthesis having a first proximal end and a first distal end, the prosthesis mounted over a distal portion of the inner elongate member;
    a stabilizing assembly for securing the first distal end of the prosthesis to the inner elongate member; and
    an introducer sheath axially movable over the prosthesis, the sheath having a second distal end positioned distal to the first distal end of the prosthesis and a second proximal end positioned proximal to the first proximal end of the prosthesis, wherein the sheath is operably connected to the drive pulley so as to allow the second proximal end of the sheath to slidably advance distally relative to the first proximal end of the prosthesis to thereby expose a proximal portion of the prosthesis.

12. The device of claim 11, further wherein the sheath is configured to retract proximally to a position where the second proximal end of the introducer sheath is aligned or disposed proximal relative to the first proximal end of the prosthesis to resheath the proximal portion of the prosthesis.

13. The device of claim 11, wherein the stabilizing assembly comprises a retaining loop assembly and a lockwire.

14. The device of claim 13, wherein the lockwire is disposed within a slot of a retaining collar portion affixed to the elongate member.

15. The device of claim 13, wherein the lockwire, the retaining loop wire, and a strut of the prosthesis interlock with each other at a predetermined location to define an anchorage point.

16. The device of claim 11, wherein the introducer sheath comprises at least one radiopaque marker affixed to a proximal end of the introducer sheath.

17. A device for delivering an intraluminal device comprising:
    a first gear set and a second gear set each being coupled to a drive shaft via on-directional roller clutch bearings, the one-directional roller clutch bearings configured to drive the first gear set when the drive shaft is rotated in one of the clockwise and counter-clockwise directions, and drive the second gear set when the drive shaft is rotated in the other of the clockwise and counter-clockwise directions;

a trigger comprising a rack engaging the main drive gear, the trigger being reciprocally movable to rotationally drive the drive shaft;

a drive pulley adapted to be alternatively mechanically coupled to the first gear set and the second gear set;

a belt coupled to the drive pulley;

an introducer sheath mechanically coupled to the belt; and an expandable prosthesis constrained within the introducer sheath, wherein the belt is configured to rotate in a clockwise direction when the drive pulley is mechanically coupled to the first gear set to distally advance the sheath beyond a proximal end of the prosthesis so as to release a proximal portion of the prosthesis from within the sheath, and further wherein the belt is configured to rotate in a counterclockwise direction when the drive pulley is mechanically coupled to the second gear set to proximally retract the sheath over the prosthesis.

18. The device of claim 17, wherein the belt is affixed to a shuttle that is axially movable therealong.

19. The device of claim 18, the introducer sheath further comprising an inner cannula, the inner cannula proximally extending from a distal tip of the device to the shuttle.

20. The device of claim 19, wherein the inner cannula axially extends within a luminal space defined by an elongate member.

* * * * *